US009155508B2

(12) United States Patent
Ueki

(10) Patent No.: US 9,155,508 B2
(45) Date of Patent: Oct. 13, 2015

(54) X-RAY CT DEVICE

(75) Inventors: Hironori Ueki, Hachioji (JP); Yukiko Ueki, legal representative, Hachioji (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 198 days.

(21) Appl. No.: 13/877,709

(22) PCT Filed: Oct. 6, 2011

(86) PCT No.: PCT/JP2011/073120
§ 371 (c)(1),
(2), (4) Date: Jul. 26, 2013

(87) PCT Pub. No.: WO2012/046813
PCT Pub. Date: Apr. 12, 2012

(65) Prior Publication Data
US 2013/0308746 A1 Nov. 21, 2013

(30) Foreign Application Priority Data

Oct. 8, 2010 (JP) .................................. 2010-228077

(51) Int. Cl.
*A61B 6/03* (2006.01)
*A61B 6/00* (2006.01)

(52) U.S. Cl.
CPC .............. *A61B 6/032* (2013.01); *A61B 6/4007* (2013.01); *A61B 6/4028* (2013.01); *A61B 6/4085* (2013.01); *A61B 6/503* (2013.01)

(58) Field of Classification Search
CPC .... A61B 6/032; A61B 6/0306; A61B 6/4014; A61B 6/4266; A61B 6/4085; A61B 6/4028; A61B 6/14; A61B 6/583; A61B 19/26; A61B 19/52; A61B 19/5212; A61B 19/5244; A61B 1/00149; A61B 1/00188; A61B 1/042; A61B 1/055; A61B 2019/5255; A61B 2019/5272; A61B 2019/5291; A61B 2019/5454; A61B 2019/548; A61N 5/1049; A61N 2005/1091; A61N 2005/105; A61N 5/103; A61N 5/1064; A61N 5/10; A61N 2005/1097; A61N 5/1045; A61N 5/1077; A61N 5/1084; A61N 2005/1059; A61N 2005/1061; A61N 5/1037; A61N 5/1067; A61N 5/1069
USPC .................................................. 378/4, 9, 147
See application file for complete search history.

(56) References Cited

U.S. PATENT DOCUMENTS 4,200,799 A * 4/1980 Saito .............................. 378/13
6,990,175 B2 * 1/2006 Nakashima et al. ............ 378/65
(Continued)

FOREIGN PATENT DOCUMENTS

JP 4-329935 11/1992
JP 9-262230 10/1997
(Continued)

OTHER PUBLICATIONS

JP Office Action of Japanese Application No. 2012-537763, issued on Apr. 22, 2014.
(Continued)

*Primary Examiner* — Irakli Kiknadze
(74) *Attorney, Agent, or Firm* — Baker Botts L.L.P.

(57) ABSTRACT

In a multi-source X-ray CT scanner having multiple X-ray sources, an imaging FOV size is fixed. In the X-ray CT scanner, a position of at least one of multiple X-ray generators is movable in the Z-axis direction (in the rotation axis direction). It is further possible to configure such that while shifting the X-ray generator, the rotation speed of the rotating plate is kept to be a predetermined value or less. Highly precise CT measurement is implemented as to various imaging FOV sizes, without exposing the test subject to ineffective radiation.

13 Claims, 19 Drawing Sheets

(56) References Cited

U.S. PATENT DOCUMENTS

| | | | |
|---|---|---|---|
| 7,542,540 B2 | 6/2009 | Matsuda | |
| 7,616,730 B2 | 11/2009 | Flohr | |
| 2008/0197303 A1* | 8/2008 | Aoi et al. | 250/522.1 |

FOREIGN PATENT DOCUMENTS

| JP | 09-262230 | 10/1997 |
|---|---|---|
| JP | 2005-143812 | 6/2005 |
| JP | 2006-122483 | 5/2006 |
| JP | 2007-44496 | 2/2007 |
| JP | 2007-044496 | 2/2007 |
| JP | 2009-297314 | 12/2009 |
| WO | WO 2009/136349 A2 | 11/2009 |

OTHER PUBLICATIONS

M. Schlindwein, Iterative three-dimensional reconstruction from twin-cone beam projections, IEEE Transactions on Nuclear Science, Oct. 1978, pp. 1135-1143, vol. NS-25, No. 5.

* cited by examiner

X-RAY CT DEVICE

TECHNICAL FIELD

The present invention relates to a medical X-ray CT scanner, and more particularly, it relates to a technique which changes an imaging field of view at high speed and appropriately in a system using a multi-focus X-ray source, so as to reduce a possibility that a test subject is exposed to ineffective radiation, and also to enhance examination throughput.

BACKGROUND ART

The X-ray CT scanner is an apparatus provided with a pair of an X-ray tube and an X-ray detector arranged in a manner being opposed to each other (hereinafter, referred to as "imaging system"), placing a test subject therebetween, taking an image of transparent X-ray data of the test subject while turning the imaging system, and reconstructing a cross-sectional image (hereinafter, referred to as a "CT image") of the test subject, and this apparatus is used widely in a field of diagnostic imaging. Upon measuring a three-dimensional region of the test subject by the X-ray CT, it is general to perform helical scanning in which the test subject is moved in the direction of the rotation axis of the imaging system, while the imaging is performed. The helical scanning is advantageous because it allows measurement within any range in the rotation axis direction. However, upon imaging the heart that needs cardiac gating, there is a problem that it is difficult to bring cardiac beats into sync with the movement of the test subject. On the other hand, in recent years, with the progress of a multi-row structure of the X-ray detector, it is now possible to measure a three-dimensional CT image, over a wide range in the rotation axis direction, by just one revolution of the imaging system. As a result, currently, an apparatus is put into practical use, which allows a scan of the test subject being kept static (hereinafter, referred to as static scanning) and measures a three-dimensional CT image of the entire heart.

In the three-dimensional CT image measured by the static scanning, there is a problem that cone-beam artifact may occur, with getting nearer both ends in the rotation axis direction, and therefore an image quality may be deteriorated. In addition, in proximity to both ends, there are some regions being irradiated with X-rays, other than the region which is able to be reconstructed as a CT image. Therefore, there is a problem that the test subject may be exposed to ineffective radiation. In order to solve the aforementioned problems, a multi-source CT utilizing multiple X-ray sources is suggested by the Non Patent Document 1, and so on.

As another example of the multi-source CT, there is an example described in the Patent Document 3, and it is already put into practical use. In this example, there are prepared two pairs of X-ray source and X-ray detector, and they are placed in such a manner as displaced by 90 degrees with respect to each other, in the rotation angle direction of the imaging system. With this configuration, imaging from the whole circumferential direction of the test subject is possible at a small rotation angle of the imaging system, and therefore there is an advantage that imaging speed can be enhanced. It is to be noted that in this example, since the focal positions of the two X-ray sources are arranged at an identical point in the rotation axis direction, it is not possible to obtain an effect to reduce the cone beam artifact simultaneously with preventing occurrence of exposure to ineffective radiation in the static scanning.

The following patent document 1 describes an example of a method for moving the position of the X-ray focus in the rotation axis direction of the imaging system. This example prevents a shift of the imaging system position in the rotation axis direction, due to thermal expansion of rotating anode of the X-ray tube. An auxiliary X-ray detector placed in proximity to the X-ray tube measures a shift quantity of the aforementioned X-ray focus position, and the entire X-ray tube is moved according to thus measured shift quantity, and the position is modified so that the shift quantity becomes zero. This keeps the position of X-ray irradiation field to be constant with respect to the X-ray detector, and therefore, there is an advantage that it is possible to prevent occurrence of exposure to ineffective radiation and deterioration of image quality in a CT image.

The following patent document 2 describes another method for preventing occurrence of exposure to ineffective radiation due to the shift of the X-ray focus position, and deterioration of image quality of a CT image. In this example, the position of a collimator that restricts the X-ray irradiation field is modified according to the shift quantity of the X-ray focus position, thereby keeping the position of the X-ray irradiation field to be constant with respect to the X-ray detector.

PRIOR ART DOCUMENT

Patent Document

Patent Document 1
Japanese Unexamined Patent Application Publication No. 2005-143812
Patent Document 2
Japanese Unexamined Patent Application Publication No. 4-329935
Patent Document 3
U.S. Pat. No. 7,616,730 B2

Non Patent Document

Non Patent Document 1
IEEE Trans. Nucl. Sci. 25, 1135-1143 (1978)

DISCLOSURE OF THE INVENTION

Problem to be Solved by the Invention

There are two X-ray focuses Sa and Sb in a multi-source CT. An axis on which these Sa and Sb are aligned is assumed as Z axis. Here, it is to be noted that the Z axis direction is identical to the rotation axis direction of an imaging system. If the positions of the two X-ray focuses Sa and Sb are fixed, it is not possible to change the size of the imaging region in the Z axis direction. Therefore, there is a problem that it is not possible to address various FOV (field of view) sizes in association with an imaging target.

An object of the present invention is directed to implementation of highly precise and high speed movement of the X-ray sources in a multi-source CT, thereby achieving precise CT measurement, without exposing a test subject to ineffective radiation.

Details as to the object and new features of the present invention are elaborated in the present specification and the accompanying drawings.

Means to Solve the Problem

In order to change the imaging region 30 depending on the imaging target, it is necessary to allow a position of an X-ray focus to be variable in the Z axis direction. In other words, the problem above may be solved by an X-ray CT scanner, including multiple X-ray generators, a collimator for restricting an irradiation range of an X-ray radiated from the X-ray generator, at least one X-ray detector for detecting the X-ray whose irradiation range is restricted, a supporter for supporting the X-ray generator and the X-ray detector, a rotation mechanism for rotating the supporter about a predetermined rotation axis, a shift mechanism for shifting in the rotation axis direction, a position of at least one X-ray generator out of the multiple X-ray generators with respect to the supporter, and a signal processor for applying signal processing on a signal detected by the X-ray detector.

Effect of the Invention

Following is a brief explanation of the effect obtained by representative examples of the present invention being disclosed by the present application.

In the multi-source X-ray CT scanner having multiple X-ray sources, highly precise CT measurement is implemented as to various imaging FOV sizes, without exposing the test subject to ineffective radiation. In addition, imaging preparation time upon changing the FOV size is reduced, thereby enhancing examination throughput.

BEST MODE FOR CARRYING OUT THE INVENTION

Hereinafter, embodiments of the present invention will be explained in detail, with reference to the accompanying drawings.

First Embodiment

Figure 1:
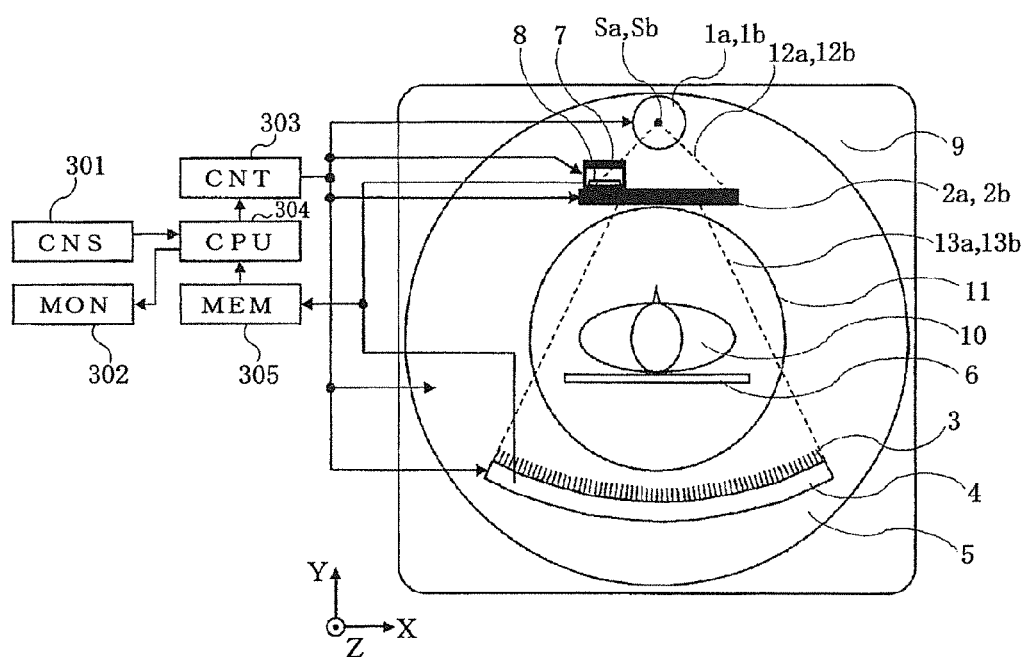
FIG. 1 is a front schematic view of the X-ray CT scanner relating to the first embodiment of the present invention.

FIG. 1 is a front schematic view of the X-ray CT scanner relating to the first embodiment of the present invention. It is to be noted here that in FIG. 1, the left-right direction, the upper-lower direction, and the vertical direction on paper, are respectively assumed as X, Y and Z directions. The X-ray CT scanner relating to the first embodiment is made up of X-ray tubes 1a and 1b, collimators 2a and 2b, an anti-scatter collimator 3, an X-ray detector 4, a rotating plate 5, abed board 6, a slit 7, an auxiliary X-ray detector 8, a gantry 9, a console (CNS) 301, a monitor (MON) 302, a controller (CNT) 303, a computer (CPU) 304, a memory (MEM) 305, and the like. The X-ray tubes 1a and 1b are installed on the rotating plate 5, in such a manner that the X-ray focuses Sa and Sb of the respective X-ray tubes are located on an identical position in the XY direction, and they are positioned at different points in the Z direction. There are also installed on the rotating plate 5, in addition to the X-ray tubes 1a and 1b, the collimators 2a and 2b, the X-ray detector 4, the anti-scatter collimator 3 fixed on the front surface of the X-ray detector 4, the slit 7, the auxiliary X-ray detector 8, and the like, and those devices are generically called as an imaging system. It is configured such that the imaging system is allowed to rotate according to the rotating plate 5. The rotating plate 5 and the imaging system are incorporated in the gantry 9.

An opening 11 is provided at the center of the gantry 9, and a test subject 10 is placed in the center of the opening 11. In the first embodiment, a human body is assumed as the test subject 10, and test subject 10 is subjected to measurement in the state being laid on the bed board 6. A drive unit not illustrated turns the rotating plate 5, thereby taking an X-ray transmission image of whole circumferential direction of the test subject 10. The rotating plate 5 rotates around the rotation axis passing through the center of the opening 11 and being parallel to the Z axis. In addition, a drive unit not illustrated may shift the position of the bed board 6 in the Z direction. It is further possible to perform a publicly known helical scanning by rotating the rotating plate 5 as described above, simultaneously with moving the bed board 6.

In FIG. 1, an example of the distance between X-ray generation points of the X-ray tubes 1a and 1b, and the X-ray input plane of the X-ray detector 4 is represented by 1,040 [mm]. In addition, an example of the diameter of the opening 11 is represented by 650 [mm]. An example of rotational speed of the rotating plate 5 is represented by 3 [revolution per second], and the imaging system takes X-ray transmission images of the test subject 10, from various rotation angles. An example of the imaging count per revolution of the imaging system is represented by 2,000 times, and one imaging is performed every time the rotating plate 5 turns by 0.18 degrees. In addition, imaging is performed by using pulsed X-rays, being radiated alternately from the X-ray tubes 1a and 1b. In other words, upon imaging, the pulsed X-rays are radiated every rotation of the rotating plate 5 by 0.18 degrees, in the following order; from the X-ray tube 1a, the X-ray tube 1b, the X-ray tube 1a, and so on. During the period when X-ray radiation is ON from one X-ray tube, X-ray radiation from the other X-ray tube is turned OFF.

The collimators 2a and 2b act as a shield in the XY plane direction and in the Z direction, against a part of the X-rays 12a and 12b respectively radiated from the X-ray tubes 1a and 1b, and then form X-ray irradiation regions 13a and 13b. As for the XY plane direction, the X-ray irradiation regions 13a and 13b are formed in such a manner as being identical to the imaging field of view of the X-ray detector 4. A method for forming the X-ray irradiation regions 13a and 13b in the Z direction will be explained later.

The auxiliary X-ray detector 8 detects the X-ray that has passed through the slit 7, out of the X-rays 12b radiated from the X-ray tube 1b. The slit 7 and the auxiliary X-ray detector 8 are placed on the end in the X direction, so that they do not block the X-rays radiated from the X-ray focus Sb and incident on the X-ray detector 4. A signal detected by the auxiliary X-ray detector 8 is utilized to calculate the position of the X-ray focus Sb in the Z direction. Detailed explanations as to the slit 7, the auxiliary X-ray detector 8, and a method for calculating the position as described above will be given later.

The X-ray detector 4 is a publicly known X-ray detector, made up of a scintillator, a photodiode, and the like. The X-ray detector 4 has a two-dimensional input plane where a large number of X-ray detection elements are arranged in matrix, and the input plane is placed in such a manner as opposed to the X-ray tubes 1a and 1b. An example of the number of elements in the matrix array is represented by 900 elements (XY plane direction)×160 elements (Z direction). The X-ray detection elements are arranged on a circular arc at approximately the same distance with respect to the X-ray generation points Sa and Sb in the XY plane. An example of each X-ray detection element in the XY plane direction and in the Z direction is represented by 1 [mm] in size.

The anti-scatter collimator 3 is a publicly known anti-scatter collimator made up of a large number of X-ray shielding plates, and it is fixed on the input plane of the X-ray detector 4. The aforementioned X-ray shielding plates are arranged in such a manner that each plate is placed between the X-ray detection elements in the XY plane direction, being vertical with respect to the input plane of the X-ray detector 4, and a large number of slits are formed in the Z direction on the input plane of the X-ray detector 4. The slit blocks an X-ray being large in incidence angle in the XY plane direction so that such X-ray does not enter the X-ray detector 4, out of the X-rays being scattered inside the test subject 10. Therefore, it is possible to prevent deterioration of precision in measurement and increase of quantum noise caused by the scattered X-rays.

Next, an explanation will be made as to an operation of the X-ray CT scanner relating to the present embodiment.

Firstly, an examiner places the test subject 10 on the bed board 6, and thereafter, sets imaging conditions via the console 301. Typical imaging conditions include, an imaging position of the test subject 10, a scanning method (selection from static scanning, step scanning, and helical scanning), a selection of source mode (single source mode, or multi-source mode), tube voltage and tube current of the X-ray tubes 1a and 1b, a rotational speed of the imaging system, and the like, and those conditions are set by using a publicly known method. Next, the examiner provides an instruction to start imaging via the console 301. Simultaneously with starting the imaging, the controller 303 starts rotation of the rotating plate 5. As for the rotation of the rotating plate 5, the rotational speed is increased until reaching a predetermined low rotational speed that will be described below, and at the point of time reaching the low rotational speed, a constant speed is maintained. The controller 303 also starts shifting the X-ray tubes 1b, simultaneously with starting rotation of the rotating plate 5, so as to move the X-ray tube 1b to a predetermined position in the Z direction, and further starts moving the bed board 6 to place the test subject 10 at a preset imaging position. Through detailed explanations will be made later, upon shifting the X-ray tube 1b as described above, firstly, the X-ray tube 1b is roughly positioned in proximity of the predetermined position, and simultaneously the collimator 2b is shielded. Next, X-rays are radiated from the X-ray tube 1b, and the auxiliary X-ray detector 8 detects the X-rays having passed through the slit 7. The memory 305 records a detection signal. The computer 304 calculates the position of the X-ray tube 1b in the Z direction, based on the aforementioned detection signal being recorded in the memory 305, and according to a result of the calculation, the controller 303 modifies the position of the X-ray tube 1b. Upon completion of both shifting the X-ray tube 1b and placing the test subject 10, the controller 303 next increases the rotational speed of the rotating plate 5 to change it to a higher rotational speed. At the point when the rotation of rotating plate 5 goes into the constant speed state, the controller 303 instructs to radiate X-rays from the X-ray tubes 1a and 1b, and to detect signals by the X-ray detector 4, and then starts imaging. During the imaging, data of the detection signals outputted from the X-ray detector 4 are sequentially stored in the memory 305. Simultaneously with the start of storing data as described above, the computer 304 uses a publicly known reconstruction algorithm to calculate a CT image of the test subject 10, and records a result of the calculation in the memory 305. In addition, the computer 304 displays thus calculated CT image on the monitor 302. A series of operations described above, from acquisition of the data to displaying of the CT image, is repeated sequentially until completing the imaging of the imaging range entirely, being designated in advance.

Figure 2:
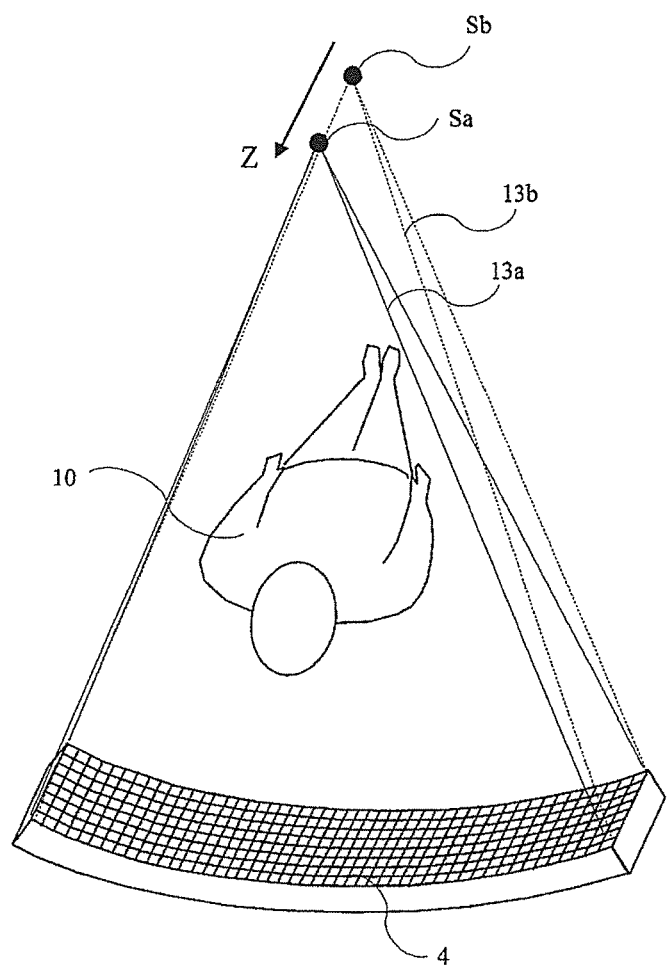
FIG. 2 is a perspective view for explaining a positional relationship between the X-ray focuses Sa and Sb, and the X-ray detector 4, in the X-ray CT scanner relating to the first embodiment of the present invention.

FIG. 2 is a perspective view for explaining a positional relationship between the X-ray focuses Sa and Sb, and the X-ray detector 4, in the X-ray CT scanner relating to the first embodiment. Drawings from FIG. 3 to FIG. 7 are side views for explaining the positional relationship between the X-ray irradiation region 13a of the X-ray focus Sa, and the X-ray irradiation region 13b of the X-ray focus Sb, in the X-ray CT scanner relating to the first embodiment. Firstly, with reference to the drawings from FIG. 2 to FIG. 7, explanations will be made as to the principle of the multi-source CT, and a positional relationship among the X-ray focuses Sa and Sb, the respective X-ray irradiation regions 13a and 13b, and the X-ray detector 4.

FIG. 2 is a perspective view for explaining a positional relationship between the X-ray focuses Sa and Sb, and the X-ray detector 4, in the multi-source CT. In the present example, two X-ray sources (X-ray tubes 1a and 1b) are arranged in such a manner as opposed to one X-ray detector 4 that has detection elements arranged in an array. The X-ray focuses Sa and Sb of the respective X-ray sources are placed at the positions different in the Z axis direction that corresponds to the rotation axis. The aforementioned X-ray focuses Sa and Sb are placed at an identical position in the direction of the rotation plane (a plane being vertical to the Z axis). The X-rays 13a and 13b respectively radiated from the X-ray focuses Sa and Sb pass through the test subject 10, and thereafter enter the X-ray detector 4.

Figure 3:
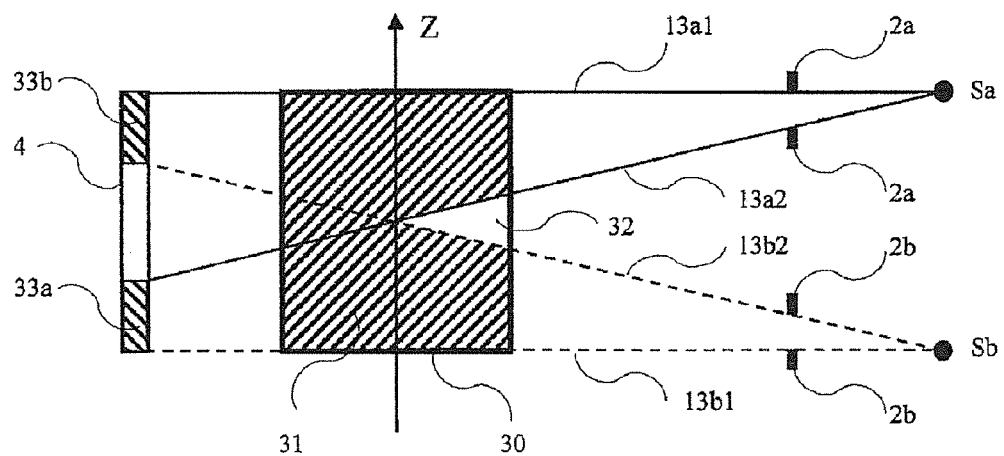
FIG. 3 is a side view for explaining one example of the positional relationship between the X-ray irradiation region 13a of the X-ray focus Sa, and the X-ray irradiation region 13b of the X-ray focus Sb, in the X-ray CT scanner relating to the first embodiment of the present invention.

FIG. 3 is a side view for explaining one example of the positional relationship between the X-ray irradiation region 13a of the X-ray focus Sa, and the X-ray irradiation region 13b of the X-ray focus Sb, in the multi-source CT. In FIG. 3, since the Z axis direction is depicted in the upper and lower direction on paper, the Z axis direction is represented as this upper and lower direction for the sake of convenience. In the present example, the X-ray focuses Sa and Sb are placed in such a manner that they correspond respectively to the upper end and the lower end positions in the Z axis direction of the X-ray detector 4. The collimators 2a and 2b respectively restrict the upper end 13a1 of the X-ray irradiation region of the X-ray focus Sa, and the lower end 13b1 of the X-ray irradiation region of the X-ray focus Sb, so as to allow the x-rays to vertically incident on the upper end and the lower end, respectively, in the Z axis direction of the X-ray detector 4. Therefore, in the present example, the imaging region is limited to the inside of the region 30, as indicated by the thick line in the figure. On the other hand, the lower end 13a2 of the X-ray irradiation region of the X-ray focus Sa, and the upper end 13b2 of the X-ray irradiation region of the X-ray focus Sb are restricted respectively by the collimators 2a and 2b in such a manner that they cross each other on the Z axis being the rotation axis of the imaging system. Radiation of X-rays is carried out at different timings in such a manner that the X-rays are not radiated simultaneously from the X-ray focuses Sa and Sb, and the X-ray detector 4 detects each of those X-rays. The timing described above is implemented by radiating pulse-like X-rays temporally, for instance, alternately from the X-ray focuses Sa and Sb. On this occasion, a non detected region 33a in which X-rays are not detected by the X-ray detector 4 is generated for the X-ray irradiation region 13a radiated from the X-ray focus Sa. In the similar manner, a non detected region 33b in which X-rays are not detected by the X-ray detector 4 is generated for the X-ray irradiation region 13b radiated from the X-ray focus Sb. In the multi-source CT of the present example, since the outside of the imaging region 30 is not irradiated with the X-rays, there is an advantage that exposure to ineffective radiation does not occur, which is a problem found in a conventional single source CT. It is to be noted that with respect to the X-ray focuses Sa and Sb in the same projection angle direction as shown in the figure, there are generated in the imaging region 30, a measurement region 31 irradiated with X-rays, and a non measurement region 32 not irradiated with X-rays.

Figure 4:
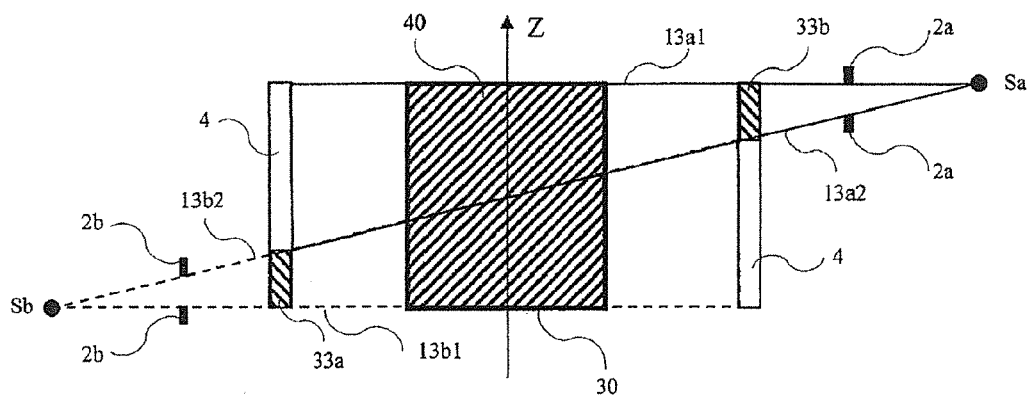
FIG. 4 is a side view for explaining the positional relationship between the X-ray irradiation region 13a of the X-ray focus Sa, and the X-ray irradiation region 13b of the X-ray focus Sb having been rotated by 180 degrees, in the X-ray CT scanner relating to the first embodiment of the present invention.

FIG. 4 is a side view for explaining the positional relationship between the X-ray irradiation region 13a of the X-ray focus Sa, and the X-ray irradiation region 13b of the X-ray focus Sb having been rotated by 180 degrees, in the multi-source CT as shown in FIG. 3. The non measurement region 32 as shown in FIG. 3 is contained in the X-ray irradiation region 13b at the position after rotating the X-ray focus Sb by 180 degrees along with rotation of the imaging system. Therefore, if all the data measured by one revolution of the imaging system is utilized, the entire area within the imaging region 30 can be measured, eventually. In addition, as described above, in the region in the vicinity of the center in the Z axis direction in the imaging region 30, it is possible to reconstruct a CT image by using information of the imaging data information radiated from both the X-ray focuses Sa and Sb. Therefore, there is an advantage that a cone beam artifact is reduced, being a problem found in a conventional single source CT.

Figure 5:
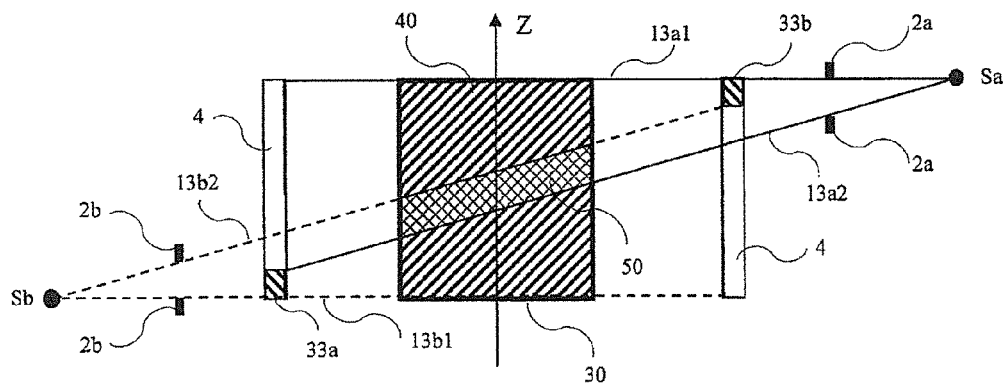
FIG. 5 is a side view for explaining the positional relationship between the extended X-ray irradiation region 13a of the X-ray focus Sa, and the extended X-ray irradiation region 13b of the X-ray focus Sb, having been rotated by 180 degrees, in the X-ray CT scanner relating to the first embodiment of the present invention.

FIG. 5 is a side view for explaining the positional relationship between the X-ray irradiation region 13a being extended of the X-ray focus Sa, and the X-ray irradiation region 13b being extended of the X-ray focus Sb having been rotated by 180 degrees, in the multi-source CT which is shown in FIG. 3. In the examples as shown in FIG. 3 and FIG. 4, the non detection regions 33a and 33b on the X-ray detector 4 are determined by the collimators 2a and 2b, in such a manner that the lower end 13a2 of the X-ray irradiation region of the X-ray focus Sa and the upper end 13b2 of the X-ray irradiation region of the X-ray focus Sb cross each other on the Z axis being the rotation axis of the imaging system. However, as shown in FIG. 5, it is further possible to change positioning of the collimators 2a and 2b in such a manner that the non detection regions 33a and 33b become narrower than the examples shown in FIG. 3 and FIG. 4. On this occasion, a region 50 is generated which is measured in overlapped manner in the imaging region 30, and this increases a region that is allowed to use the imaging data information radiated from both the X-ray focuses Sa and Sb to reconstruct a CT image. Therefore, it is possible to expand the region where the cone-beam artifact is reduced.

As explained with reference to FIG. 2 to FIG. 5 so far, there is found an advantage that in the multi-source CT, exposure to ineffective radiation in the static scanning does not occur any more, and simultaneously the cone-beam artifact is reduced, which are problems in the conventional single source CT.

Figure 6:
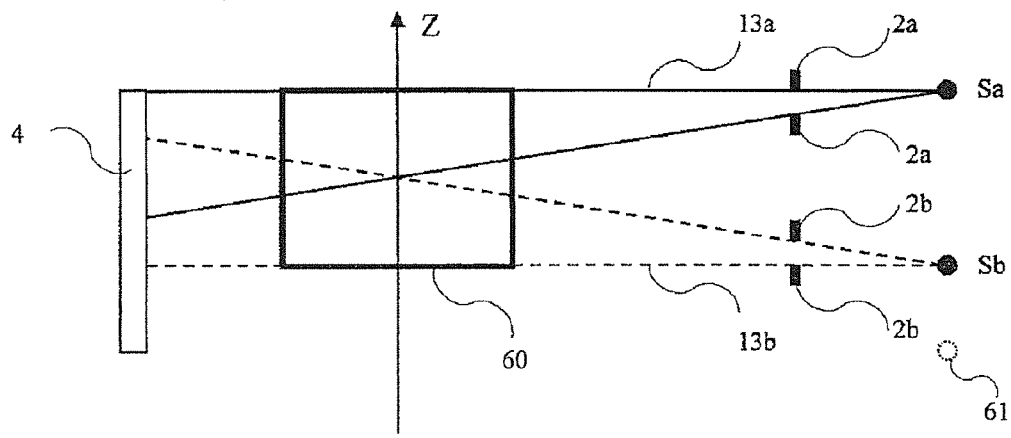
FIG. 6 is a side view for explaining the positional relationship between the X-ray focus Sb and the imaging region 60, in the case where the position of the X-ray focus Sb in the Z axis direction has been changed in the X-ray CT scanner relating to the first embodiment of the present invention.

It is to be noted that the X-ray CT scanner relating to the first embodiment is provided with a function for shifting the position of the X-ray focus Sb in the Z axis direction as shown in FIG. 6. Here, a detailed explanation will be made as the following; FIG. 6 is a side view for explaining the positional relationship between the X-ray focus Sb and the imaging region 60, in the case where the position of the X-ray focus Sb in the Z axis direction is changed in the multi-source CT as shown in FIG. 3. In this figure, the position of the X-ray focus Sb in the Z axis direction is shifted upwardly, relative to the initial position 61. As illustrated, the width of the imaging region 60 in the Z axis direction becomes equal to the distance between the X-ray focuses Sa and Sb. Therefore, by setting the position of the X-ray focus Sb as variable, it is possible to freely change the width of the imaging region 60 in the Z axis direction, depending on the imaging target.

On the other hand, also in the multi-source CT, it is conceivable that there emerges a need for performing the conventional single source imaging which utilizes one X-ray focus, in some cases. In the case where the position of the X-ray focus Sb in the Z axis direction is set to be variable, there is another advantage that it is possible to reduce the cone-beam artifact in the single source imaging, which will be described below.

Figure 7:
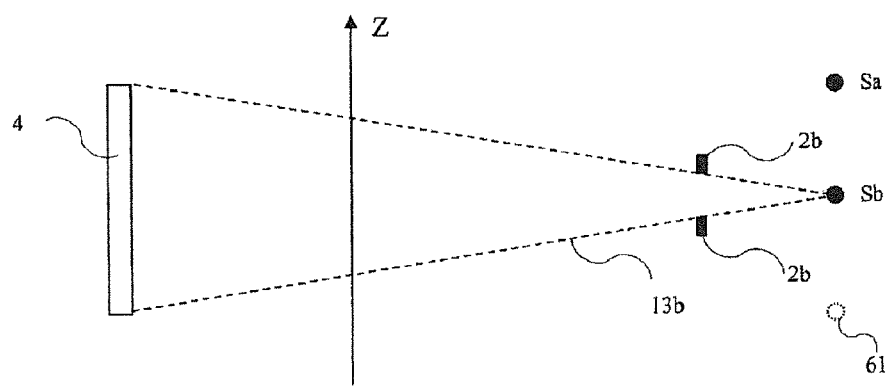
FIG. 7 is a side view for explaining the positional relationship between the X-ray irradiation region 13b and the X-ray detector 4, when a single source imaging is performed using only the X-ray focus Sb, in the X-ray CT scanner relating to the first embodiment of the present invention.

As shown in FIG. 7, there is provided an imaging function for single source scanning using only the X-ray focus Sb. Here, a detailed explanation will be made as the following; FIG. 7 is a side view for explaining the positional relationship between the X-ray irradiation region 13b and the X-ray detector 4, when the single source imaging is performed using only the X-ray focus Sb in the multi-source CT as shown in FIG. 3. In the case where the single source imaging is performed in the multi-source CT, it is also possible to take an image, keeping the X-ray focus Sb at the initial position 61. However, in this case, the distance between the X-ray focus Sb and the upper end of the X-ray detector 4 becomes longer, and therefore, there occurs a problem that the cone beam artifact becomes larger in the CT image at the upper position in the Z axis direction. On the other hand, as illustrated in the figure, if the position of the X-ray focus Sb in the Z axis direction is placed in the center of the field of view of the X-ray detector 4, the distance between the X-ray focus Sb and both ends of the X-ray detector 4 becomes shorter, and therefore there is an advantage that it is possible to reduce deterioration of image quality, which is caused by the cone-beam artifact.

As discussed above, in the multi-source CT, in order to change the imaging region in the Z axis direction depending on an imaging target, or to reduce the cone-beam artifact in the single source imaging, it is necessary to provide a mechanism to set the position in the Z-axis direction to be variable, as to at least one X-ray focus. Means for solving the problems above are collectively described in the following.

(Means 1)

An X-ray CT scanner includes multiple X-ray generators, a collimator for restricting an irradiation range of X-rays radiated from the X-ray generator, at least one X-ray detector for detecting the X-rays whose irradiation range is restricted, a supporter for supporting the X-ray generators and the X-ray detector, a rotation mechanism for rotating the supporter about a rotation axis, a shifting mechanism for shifting in a direction of the rotation axis, a position of at least one X-ray generator out of the multiple X-ray generators, with respect to the supporter, and a signal processor for applying signal processing on a signal detected by the X-ray detector. Accordingly, in the multi-source CT, it is possible to implement shifting of an X-ray source with high precision and at a high speed, thereby achieving a highly precise CT measurement without exposing a test subject to ineffective radiation.

As a method for implementing the shift of the X-ray focus in the Z axis direction, there is a method for providing a mechanism to move the entire X-ray source in the Z axis direction, as described in the Patent Document 1, for instance. However, if the method as described in the aforementioned Patent Document 1 is employed, following problems may occur.

Problem 1:

In the example of the Patent Document 1, the X-ray source is moved, in order to correct a shift of the X-ray focus position caused by thermal expansion of the X-ray tube rotating anode. A moving stroke necessary for this occasion is a few hundreds of micrometers at the most, whereas the multi-source CT requires the moving stroke to be a few centimeters or dozens of centimeters. Accordingly, since a travel distance is considerably long and it takes time for the shift, resulting in that throughput of the examination is lowered. The moving stroke is long in the multi-source CT, because as shown in FIG. 6 and FIG. 7, it is necessary to change the imaging range depending on the imaging target, and a range for the change may cover a few centimeters to dozens of centimeters.

Problem 2:

Displacement of the X-ray focus may expose the test subject to ineffective radiation, or may cause generation of an artifact in the CT image. Therefore, similar to the example of the Patent Document 1, the multi-source CT also requires a high positional precision in shifting the X-ray focus, and generally, it is necessary to set a tolerance to be plus or minus dozens of micrometers.

Problem 3:

In order to enhance the examination throughput, it is conceivable to provide a method that performs approach rotation of the imaging system during the imaging preparation period, simultaneously with shifting the X-ray source, thereby reducing the imaging preparation period. However, rotation of the imaging system generates a large centrifugal force on the X-ray source, and therefore, a large drive force is required for the shift.

The X-ray source shifting mechanism as described in the Patent Document 1 employs a shifting stage that is typically driven by a stepping motor, or the like. On this occasion, in order to achieve high-speed shifting and high drive force as countermeasures against the problems 1 and 3, a large-sized motor is necessary, and therefore it is difficult to reduce cost and save space. In order to achieve high precision as a countermeasure against the problem 2, high speed shifting is difficult. A summary of the means for solving those problems above is collectively described in the following.

(Means 2)

An X-ray CT scanner includes multiple X-ray generators, a collimator for restricting an irradiation range of the X-rays radiated from the X-ray generator, at least one X-ray detector for detecting the X-rays whose irradiation range is restricted, a supporter for supporting the X-ray generators and the X-ray detector, a rotation mechanism for rotating the supporter about a predetermined rotation axis, a shifting mechanism for shifting in the rotation axis direction, a position of at least one X-ray generator out of the multiple X-ray generators, with respect to the supporter, and a signal processor for applying signal processing on a signal detected by the X-ray detector, and generating a CT image of a test subject based on the X-ray transmission images of the test subject taken from different angles, the X-ray CT scanner being provided with a function for keeping a speed of rotation by the rotation mechanism, to a predetermined value or less during a period of shifting by the shifting mechanism. With this configuration, the centrifugal force applied to the X-ray generator during the period when the X-ray generator is shifting is allowed to be a value smaller than a predetermined value, and this allows the X-ray generator to shift at high speed by using the shifting mechanism being relatively small in size. In addition, rotation according to the rotation mechanism and shifting according to the shifting mechanism are performed concurrently, and further, after completion of the shift according to the shifting mechanism, the speed of rotation is allowed to be changed to a higher speed immediately. Therefore, the time required for the imaging preparation period is reduced, and thereby enhancing the examination throughput.

(Means 3)

The X-ray CT scanner as described in the means 2 is further provided with a function for selecting and designating a position of the X-ray generator, out of given multiple preset positions, the position being changed by the shifting mechanism. With this configuration, the examiner is allowed to select a desired imaging field of view, out of multiple imaging fields of view being preset, thereby simplifying setting of the imaging conditions, which is executed by the examiner.

(Means 4)

The X-ray CT scanner as described in the means 3 is further provided with a function for designating an imaging region of the test subject prior to imaging, and a function for automatically selecting a preset position which implements a minimum imaging field of view covering the imaging region, out of the multiple preset positions. With this configuration, the examiner only designates a desired imaging region, so as to achieve automatic selection of optimum imaging field of view, thereby simplifying setting of the imaging conditions, which is executed by the examiner.

(Means 5)

The X-ray CT scanner as described in the means 3 is further provided with a recording part for recording an X-ray calibration signal measured in advance at the preset position of the X-ray generator. With this configuration, it is possible to utilize an optimum X-ray calibration data measured in advance at each preset position of the X-ray generator, and therefore, generation of artifact can be prevented in the X-ray CT image, caused by using inappropriate calibration data.

(Means 6)

The X-ray CT scanner as described in the means 2 and 3 includes an auxiliary X-ray detector for detecting the X-rays radiated from the X-ray generator in proximity to the preset position, further provided with a function for calculating an amount of displacement from the preset position of the X-ray generator based on a detection signal of the auxiliary X-ray detector, and a function for modifying the position of the X-ray generator based on the amount of displacement. With this configuration, it is possible to modify the position of the X-ray generator to an accurate position during the imaging of the test subject, and therefore, it is possible to prevent exposure to ineffective radiation and generation of artifact in the CT image caused by the displacement of the X-ray generator.

(Means 7)

The X-ray CT scanner as described in the means 6 is provided with a function for blocking an X-ray irradiation on the test subject, by closing the collimator until the amount of displacement becomes smaller than a predetermined value. With this configuration, it is possible to modify the position of the X-ray generator to an accurate position, prior to imaging the test subject, and thereby preventing exposure to ineffective radiation and generation of artifact in the CT image, caused by the displacement of the X-ray generator.

(Means 8)

The X-ray CT scanner as described in the means 2 and 3 includes an auxiliary X-ray detector for detecting the X-rays radiated from the X-ray generator in proximity to the preset position, further provided with a function for calculating an amount of displacement from the preset position of the X-ray generator based on a detection signal of the auxiliary X-ray detector, and a function for modifying the position of the collimator based on the amount of displacement, so that an irradiation range of the X-rays radiated from the X-ray generator on the X-ray detector is placed at a predetermined position. With this configuration, even in the case where shifting of the X-ray generator by the shifting mechanism is difficult because rotation by the rotation mechanism is high speed, it is possible to correct the displacement of the X-ray irradiation range due to the position displacement of the X-ray generator, and thereby preventing exposure to ineffective radiation and generation of artifact in the CT image.

(Means 9)

The X-ray CT scanner as described in the means 6 and 8 is further provided with the auxiliary X-ray detectors individually at the multiple preset positions respectively. With this configuration, it is possible to measure with a high degree of precision, the displacement of the X-ray generator as to each of all the preset positions, and modify the position.

(Means 10)

The X-ray CT scanner as described in the means 6 and 8 is further provided with the auxiliary X-ray detector commonly for a part of or all of the multiple preset positions. With this configuration, it is possible to bring production costs down by decreasing the number of the auxiliary X-ray detectors and/or the areas thereof.

(Means 11)

The X-ray CT scanner as described in the means 3 is further provided with a function for controlling the position of the collimator so that a non-irradiation range is provided in a part of the X-ray irradiation range in which the test subject is irradiated in overlapped manner by the multiple X-ray generators, thereby restricting the X-ray irradiation range, a function for calculating an amount of displacement of the position of the X-ray generator from the preset position, based on signals detected respectively in the X-ray irradiation range and in the non-irradiation range on the X-ray detector, and a function for modifying the position of the X-ray generator based on the amount of displacement. With this configuration, it is possible to correct the position of the X-ray generator to an accurate position, without using the auxiliary X-ray detector, and therefore, exposure to ineffective irradiation and generation of artifact in the CT image caused by the displacement of the X-ray detector can be prevented, with bringing the production costs down.

(Means 12)

The X-ray CT scanner as described in the means 3 is further provided with a function for controlling the position of the collimator so that a non-irradiation range is provided in a part of the X-ray irradiation range in which the test subject is irradiated in overlapped manner by the multiple X-ray generators, thereby restricting the X-ray irradiation range, a function for calculating an amount of displacement of the position of the X-ray generator from the preset position, based on signals detected respectively in the X-ray irradiation range and in the non-irradiation range on the X-ray detector, and a function for modifying the position of the collimator based on the amount of displacement, so that the X-ray irradiation range radiated from the X-ray generator to the X-ray detector is placed at a predetermined position. With this configuration, even in the case where shifting of the X-ray generator by the shifting mechanism is difficult because rotation by the rotation mechanism is high speed, it is possible to modify the displacement of the X-ray irradiation range due to the position displacement of the X-ray generator, without using the auxiliary X-ray detector. Therefore, exposure to ineffective radiation and generation of artifact in the CT image can be prevented, with bringing the production costs down.

(Means 13)

The X-ray CT scanner as described in the means 2 is further provided with a function for controlling the position of the collimator so that a non-irradiation range is provided in a part of the X-ray irradiation range in which the test subject is irradiated in overlapped manner by the multiple X-ray generators, thereby restricting the X-ray irradiation range, and a function for calculating and eliminating an amount of scattered X-ray component included in the signal detected in the X-ray irradiation range, based on the signal detected in the non-irradiation range out of the detection signals of the X-ray detector. With this configuration, it is possible to eliminate the scattered X-ray component included in the X-ray irradiation range, and therefore, fluctuations of the CT value in the CT image which are caused by the scattered X-rays and generation of artifact can be reduced.

Figure 8:
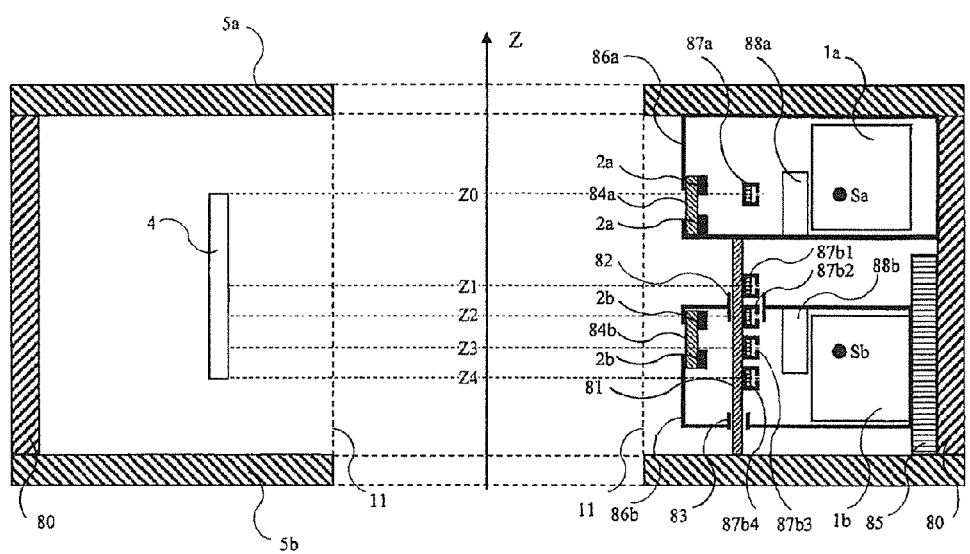
FIG. 8 is a side sectional view for explaining a structure of the imaging system of the X-ray CT scanner relating to the first embodiment of the present invention.
Figure 9:
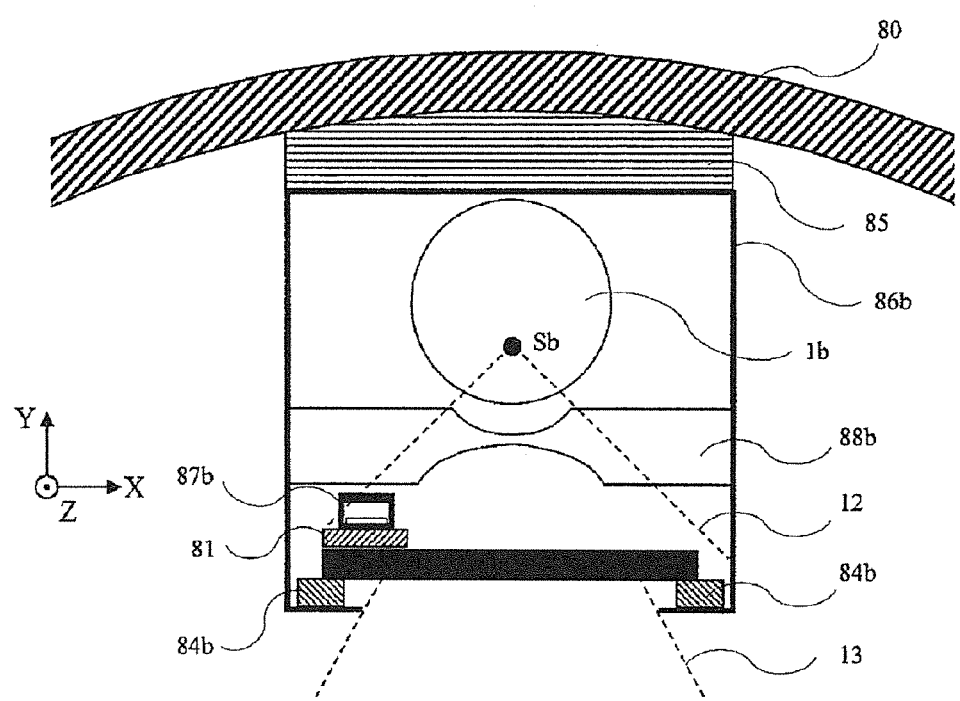
FIG. 9 is a front sectional view at the position of the X-ray tube 1b, for explaining a structure of the imaging system of the X-ray CT scanner relating to the first embodiment.

FIG. 8 is a side sectional view for explaining a structure of the imaging system of the X-ray CT scanner relating to the first embodiment. FIG. 9 is a front sectional view at the position of the X-ray tube 1b, for explaining a structure of the imaging system of the X-ray CT scanner relating to the first embodiment. The rotating plate 5 as shown in FIG. 1 has a two-layered structure including the rotating plates 5a and 5b, and both are arranged in such a manner as placing therebetween, both edge faces of the drum-type frame 80 having a circular cylindrical shape. The X-ray tubes 1a and 1b are respectively fixed on the inside of the X-ray tube supporting frames 86a and 86b, and the X-ray tube supporting frame 86a is fixed inside the rotating plate 5a and the drum-type frame 80. The X-ray tube supporting frame 86b is installed on the movable stage 85, and the movable stage 85 is fixed inside the drum-type frame 80. The movable stage 85 is a publicly known movable stage made up of a motor not illustrated and a movable table, and it moves the entire X-ray tube supporting frame 86b in the Z axis direction. Beam compensation filters 88a and 88b are fixed respectively inside the X-ray tube supporting frames 86a and 86b. The beam compensation filters 88a and 88b are publicly known filters used for compensating for changes in energy spectrum when the X-rays radiated from the X-ray tubes 1a and 1b pass through the test subject 10.

In addition, publicly known movable stages 84a and 84b are fixed respectively inside the X-ray tube supporting frames 86a and 86b. Each of the movable stages 84a and 84b is provided with a function for changing the position in the Z axis direction and the open width of the collimators 2a and 2b, the collimators also being placed respectively inside the X-ray tube supporting frames 86a and 86b.

Figure 13:
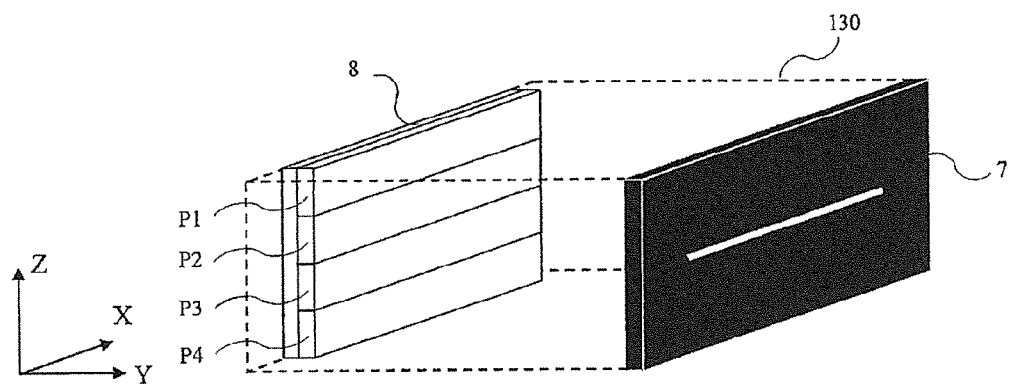
FIG. 13 illustrates an internal configuration of a position detection unit 87 in the X-ray CT scanner relating to the first embodiment.

A position detection unit 87a is placed inside the X-ray tube supporting frame 86a. As shown in FIG. 13, the position detection unit 87a is made up of the slit 7, the auxiliary X-ray detector 8, the frames for supporting those elements, and the like. A shift in position of the X-ray focus Sa in the Z axis direction along with thermal expansion of the rotating anode of the X-ray tube 1a is calculated according to the method as described in the following, based on a detection signal of the position detection unit 87a. In addition, on the basis of the aforementioned calculation result, the position of the collimator 2a is modified so as to obtain adequate irradiation position of the X-ray radiated from the X-ray focus Sa.

On the upper surface and lower surface of the X-ray tube supporting frame 86b, there are provided holes 82 and 83 respectively, for allowing penetration of the position detection unit supporting frame 81. Both ends of the position detection unit supporting frame 81 are respectively fixed on the X-ray tube supporting frame 86a and the rotating plate 5b. Four position detection units 87b1 to 87b4 are arranged at different positions in the Z-direction, on the position detection unit supporting frame 81. In the X-ray CT scanner relating to the first embodiment, there are prepared four positions Z1 to Z4 being preset in advance, as the positions in the Z-direction of the X-ray focus Sb, and the examiner is allowed to select a desired position depending on an imaging target, according to the method described below. Basically, it is not necessary to move both X-ray focuses, but by moving both of them simultaneously, there is an advantage such as achieving high-speed shifting. Therefore, a supplemental explanation is added in the last part of the embodiments of the present invention.

The position detection units 87b1 to 87b4 are arranged respectively in association with the preset positions Z1 to Z4, and they are used to measure the displacement of the X-ray focus Sb from each of the preset positions. In the present embodiment, in particular, the preset position Z4 is positioned at a lower end in the Z direction of the X-ray detector 4, and the preset position Z1 is positioned at the center in the Z direction of the X-ray detector 4. In addition, the preset positions Z2 and Z3 are arranged in such a manner as equally dividing the distance between the aforementioned Z1 and Z4, but the number of the preset positions and the arrangement thereof are not limited to the present example. It is to be noted that when multi-source imaging is performed at the preset positions Zn (n=1 to 4), the scan width corresponding to the imaging field of view in the Z direction is expressed by Dn=(Z0−Zn). Here, Z0 is a position of the X-ray focus Sa in the Z axis direction.

Figure 10:
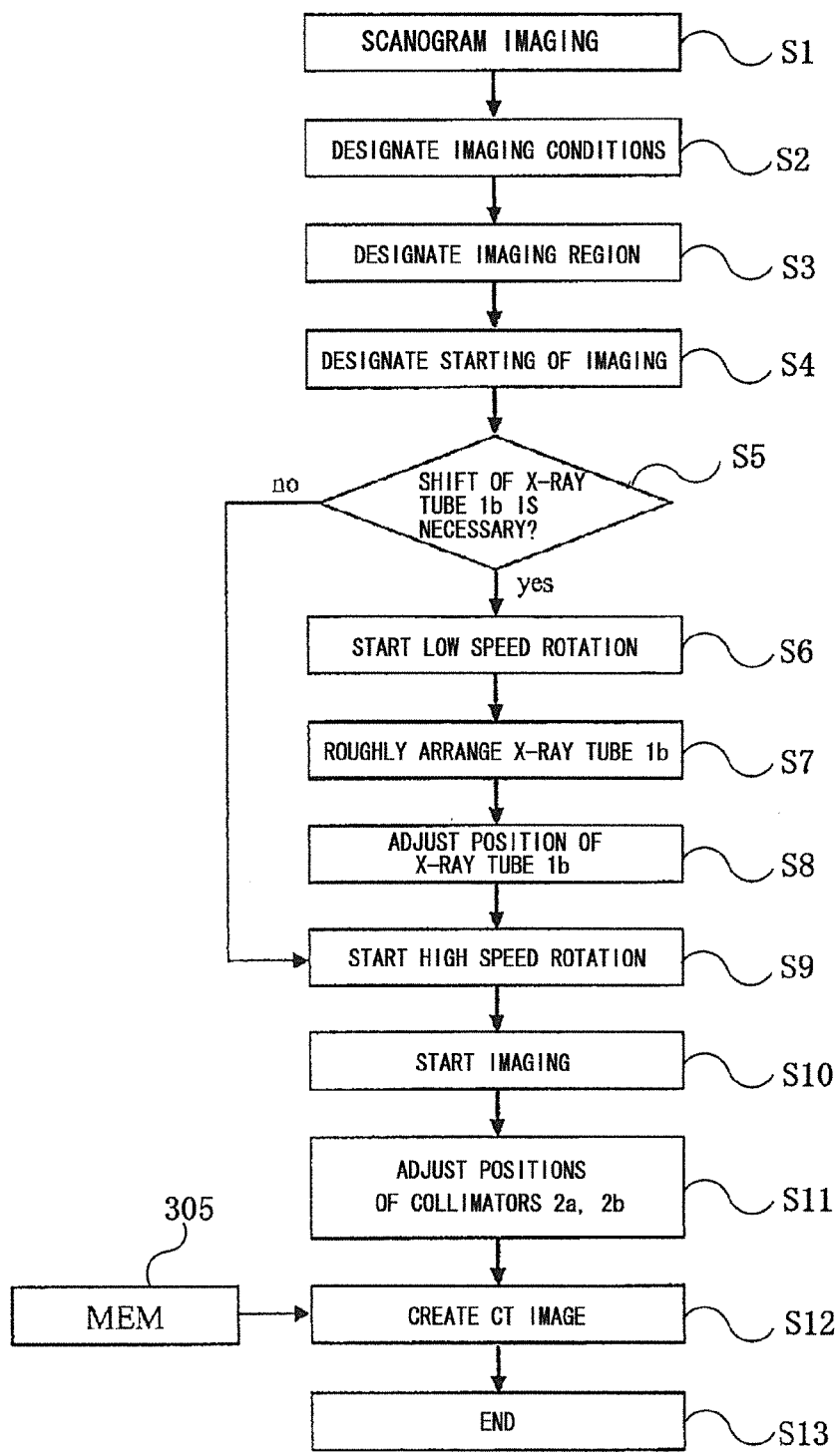
FIG. 10 is a flowchart for explaining an imaging procedure of the X-ray CT scanner relating to the first embodiment.

FIG. 10 is a flowchart for explaining an imaging procedure of the X-ray CT scanner relating to the first embodiment. Hereinafter, the imaging procedure will be explained with reference to this flowchart. Prior to the CT imaging, a publicly known scanogram imaging is performed (step S1). The scanogram imaging is performed by moving the bed board 6 in the Z direction on which the test subject 10 is placed, keeping the static state without rotating the imaging system, and measuring an X-ray transmission image of the test subject 10. Next, the examiner uses a setting screen displayed on the monitor 302 to designate imaging conditions via the console 301 (step S2). Major imaging conditions designated in the step S2 may include, a selection of the scanning method (static scanning, step scanning, or helical scanning), a selection of source mode (single source mode or multi-source mode), setting of the scan width, setting of tube voltage and tube current of the X-ray tube, setting of rotational speed of the imaging system, and the like. It is to be noted that the scan width corresponds to the imaging field of view in the Z direction of the X-ray detector 4, and in the multi-source mode, the scan width Dn (n=1 to 4) is determined according to the preset position as described above.

Next, the examiner uses the image of scanogram displayed on the monitor 302 to designate an imaging region via the console 301 according to the method described below (step S3). Then, the examiner designates starting CT imaging via the console 301 (step S4). On this occasion, the computer 304 determines whether or not shifting of the X-ray tube 1b to the preset position is necessary (step S5), and if it is necessary, low-speed rotation of the imaging system is started (step S6). On the other hand, if it is not necessary, high-speed rotation of the imaging system is started (step S9).

In proceeding with the step S6, the rotation of the rotating plate 5 is gradually accelerated, and at the time of reaching a predetermined low rotational speed, this rotational speed is maintained. It is to be noted that an example of the rotational speed of the low-speed rotation is represented by 0.5 [revolution/second]. In the step S6, simultaneously with starting the rotation of the imaging system, the movable stage 85 next moves the X-ray tube 1b to a predetermined preset position, and roughly places it thereon (step S7). In the aforementioned placement, there is a possibility that the X-ray focus Sb may be displaced from a certain preset position, due to insufficient positioning precision of the movable stage and/or a shift in position of the X-ray focus Sb in the Z-axis direction, caused by the thermal expansion of the rotating anode of the X-ray tube 1b. Therefore, in order to modify the aforementioned displacement of the X-ray focus Sb, position adjustment is performed on the X-ray tube 1b, subsequently (step S8). It is to be noted that a method of the position adjustment will be described in detail later.

Upon completion of the position adjustment of the X-ray tube 1b, high-speed rotation of the imaging system is started next (step S9). An example of the rotational speed of the high-speed rotation is represented by 3 [revolution/second]. At the time when the imaging system reaches a predetermined high-speed rotation, imaging is started next (step S10). During the imaging, a part of the X-rays radiated from the X-ray tubes 1a and 1b is detected by the position detection units 87a and 87b, and the computer 304 calculates an amount of the position shift in the Z axis direction of the X-ray focuses Sa and Sb due to the thermal expansion of the rotating anode. In addition, on the basis of the calculation result above, the positions of the collimators 2a and 2b are modified according to the method described below (step S11). It is to be noted that during the X-rays are irradiated in the imaging, the process of the step S11 above is repeated over and over again, and the position displacement of the X-ray focuses Sa and Sb is modified at any time. The imaging data is sequentially stored in the memory 305. The computer 304 reads the imaging data sequentially from the memory 305, and creates a CT image according to the procedure as described below (step S12). Finally, at the time when the measurement of the entire imaging region is completed, the X-ray radiation is stopped and imaging is completed (step S13).

As discussed above, in the X-ray CT scanner relating to the first embodiment, the rotational speed of the imaging system is kept low during the time when the X-ray tube 1b is moving to the preset position, and therefore, the centrifugal force applied to the X-ray tube 1b can be controlled to be a predetermined value or less. Therefore, it is possible to downsize the drive mechanism of the movable stage 85, thereby achieving lower cost and higher speed in shifting. In addition, since it is possible to immediately transfer from the low speed rotation during the imaging preparation to the high speed rotation during the imaging, the imaging preparation time can be reduced, thereby enhancing the imaging throughout.

Figure 11:
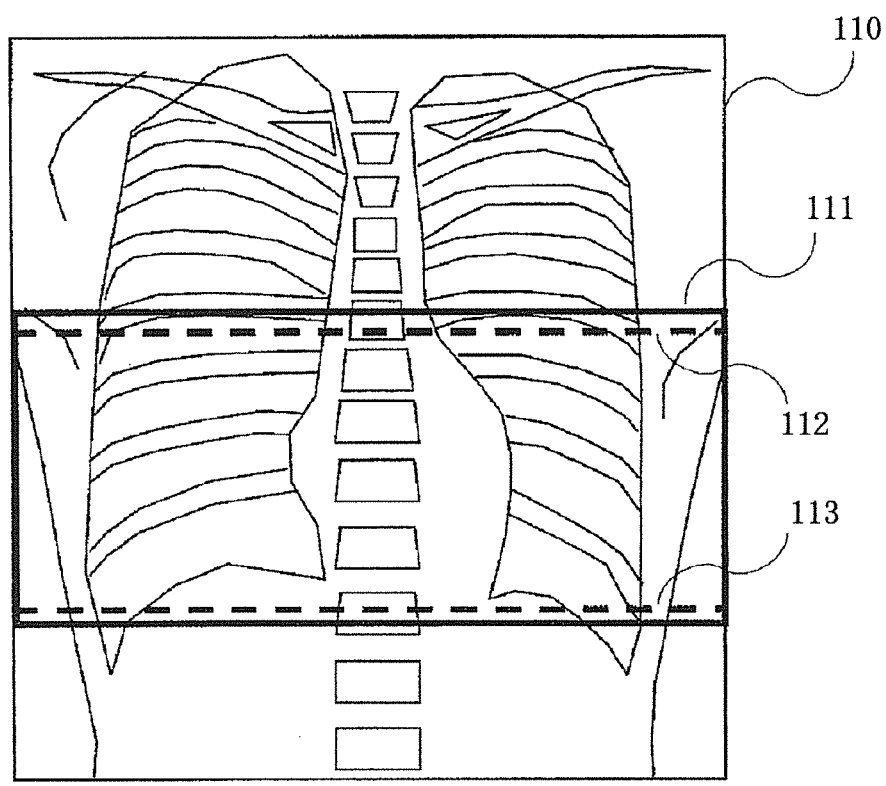
FIG. 11 illustrates a method for designating an imaging region in the X-ray CT scanner relating to the first embodiment.

FIG. 11 illustrates a method for designating an imaging region in the X-ray CT scanner relating to the first embodiment. Particularly, this figure illustrates a specific method for implementing the process of step S3 in the flowchart as shown in FIG. 10. The scanogram image 110 of the test subject 10 acquired in the step S1 of FIG. 10 is displayed on the monitor 302. The examiner is allowed to designate an upper end position 112 and the lower end position 113 of a desired imaging region via the console 301, while viewing the scanogram image 110. On this occasion, if the static scanning mode and multi-source mode are selected in setting the imaging conditions in the step S2, the computer 304 calculates an imaging region having a minimum scan width Dn covering the entire desired imaging region, and displays the imaging region on the scanogram image 110 as an imaging region candidate 111. If there is no scan width covering the entire desired imaging region, an imaging region having a maximum scan width D4 is displayed on the scanogram 110 as the imaging region candidate. The examiner is allowed to change the position of the imaging region variously based on the imaging region candidate 111 being displayed. If necessary, it is also possible to return to the step S2 to change the imaging conditions, such as the scanning method, source mode, scan width, and the like.

Figure 12:
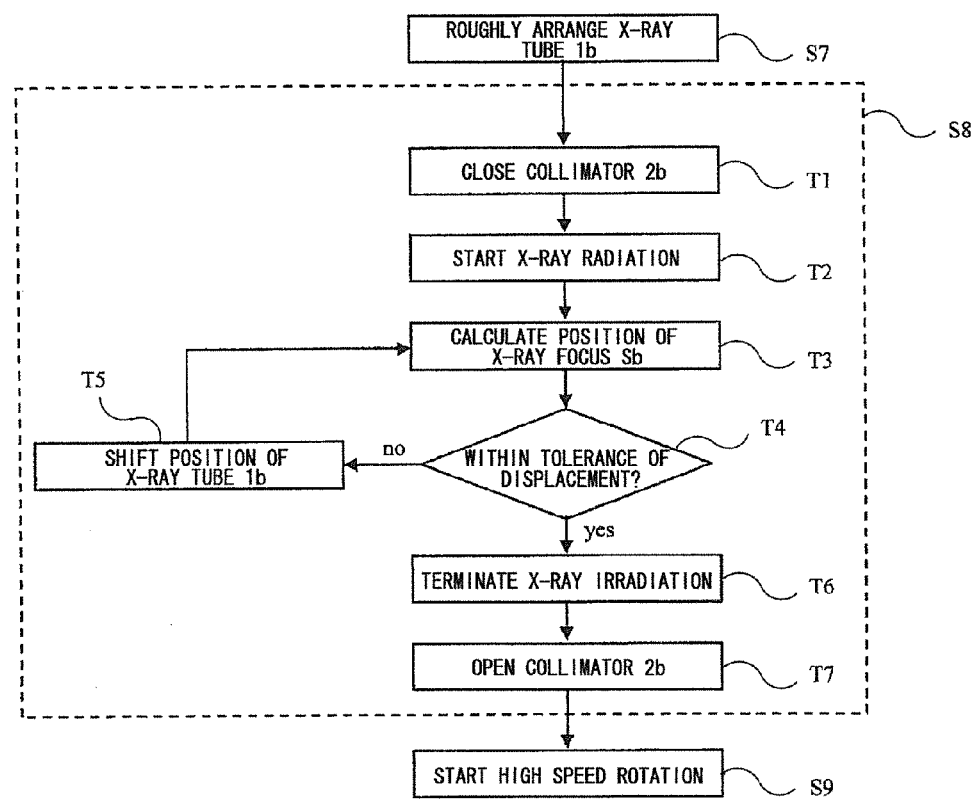
FIG. 12 is a flowchart for explaining a procedure for adjusting the position of the X-ray tube 1b in the X-ray CT scanner relating to the first embodiment.

FIG. 12 is a flowchart for explaining a procedure for adjusting the position of the X-ray tube 1b in the X-ray CT scanner relating to the first embodiment. Particularly, this figure illustrates a specific method for implementing the process of the step S8 in the flowchart as shown in FIG. 10. After completing the rough arrangement of the X-ray tube 1b in the step S7, firstly, the movable stage 84 is moved and the collimator 2b is closed (step T1). This is performed for the purpose of shielding against the X-rays so as to prevent the test subject 10 from being exposed to radiation, in the X-ray irradiation for measuring the position of the X-ray focus Sb which is performed subsequently.

Next, radiation of X-rays is started (step T2). On this occasion, the signal detected by the position detection unit 87 is recorded in the memory 305, and the computer 304 calculates the position of the X-ray focus Sb according to the method described below, based on the detection signal recorded in the memory 305 (step T3). Next, the computer 304 calculates a displacement of the X-ray focus Sb from the given preset position based on a result of the above calculation, and determines whether or not the amount of displacement is within a tolerance (step T4). It is to be noted that an example of the tolerance above is represented by 50 [μm]. If the amount of the displacement is not within the tolerance, the computer modifies the displacement by shifting the position of the X-ray tube 1b (step T5), and thereafter returning to the step T3, and then, recalculates the position of the X-ray focus Sb.

If the amount of the displacement is within the tolerance in the step T4, the radiation of X-rays is terminated (step T6). Subsequently, the collimator 2b being closed in the step T1 is reopened (step T7), thereafter transferring to the high-speed rotation in the step S9. It is to be noted that in the procedure of the present flowchart, after modifying the displacement of the X-ray tube 1b in the step T5, the process returns to the step T3, but alternatively, it is possible to proceed with T6 in order to reduce the imaging preparation period.

FIG. 13 illustrates an internal configuration of the position detection unit 87 in the X-ray CT scanner relating to the first embodiment. The position detection unit 87 is made up of the slit 7, the auxiliary X-ray detector 8, the frame 130 supporting those elements, and the like. The slit 7 is publicly known as a shield against the X rays incident on a region other than the slit, and it is arranged in such a manner that the longitudinal direction of the slit is parallel to the X direction. In addition, the auxiliary X-ray detector 8 is a publicly known array-type X-ray detector having the detection elements P1 to P4 in four rows parallel to the Z direction. The detection elements P1 to P4 in four rows detect a distribution in the Z direction of X rays which have passed through the slit 7.

Figure 14:
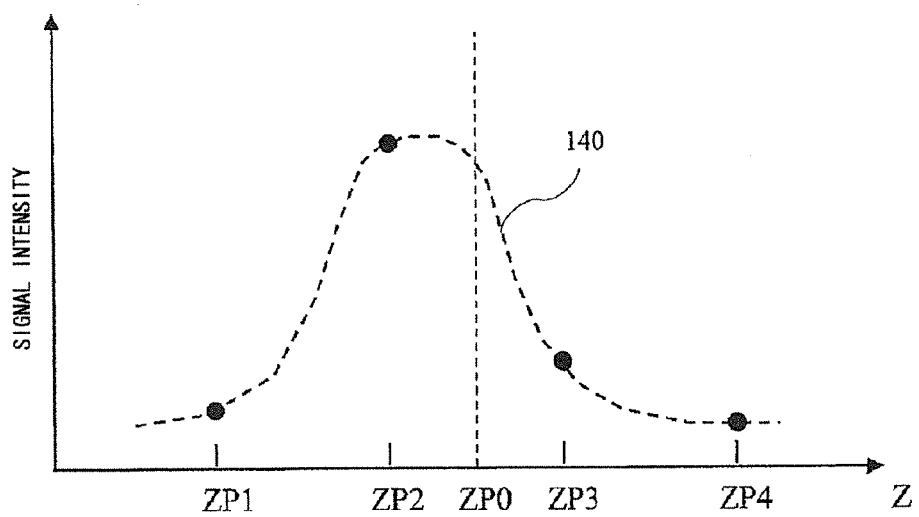
FIG. 14 illustrates one example of a detection signal of the position detection unit 87 in the X-ray CT scanner relating to the first embodiment.

FIG. 14 illustrates one example of a detection signal of the position detection unit 87 in the X-ray CT scanner relating to the first embodiment. If the position of the X-ray focus Sb is displaced in the Z direction from the original preset position ZP0, an X-ray distribution 140 passed through the slit 7 and incident on the auxiliary X-ray detector 8 is left-right asymmetrical with respect to ZP0. Therefore, it is possible to calculate the amount of displacement ΔZ of the X-ray focus Sb from the preset position ZP0, based on the X-ray distribution 140. By way of example, it is possible to calculate ΔZ using the following formula 1.

$$\Delta Z = -ZG \cdot DX/dX \quad \text{[Formula 1]}$$

It is to be noted that DX represents a distance between the X-ray focus Sb and the slit 7 in the X direction, dX represents a distance between the slit 7 and the input plane of the auxiliary X-ray detector 8 in the X direction. In addition, ZG represents the barycentric position of the X-ray distribution 140 in the Z direction, and it is computed according to the formula 2.

$$ZG = \sum_{n=1}^{4} (ZP_n - ZP_0) q_n \Big/ \sum_{n=1}^{4} q_n \quad \text{[Formula 2]}$$

Here, $ZP_n$ (n=1 to 4) represents the position of the detection element $P_n$ in the Z direction, and $q_n$ represents a detection signal of the detection element $P_n$ (n=1 to 4).

Figure 15:
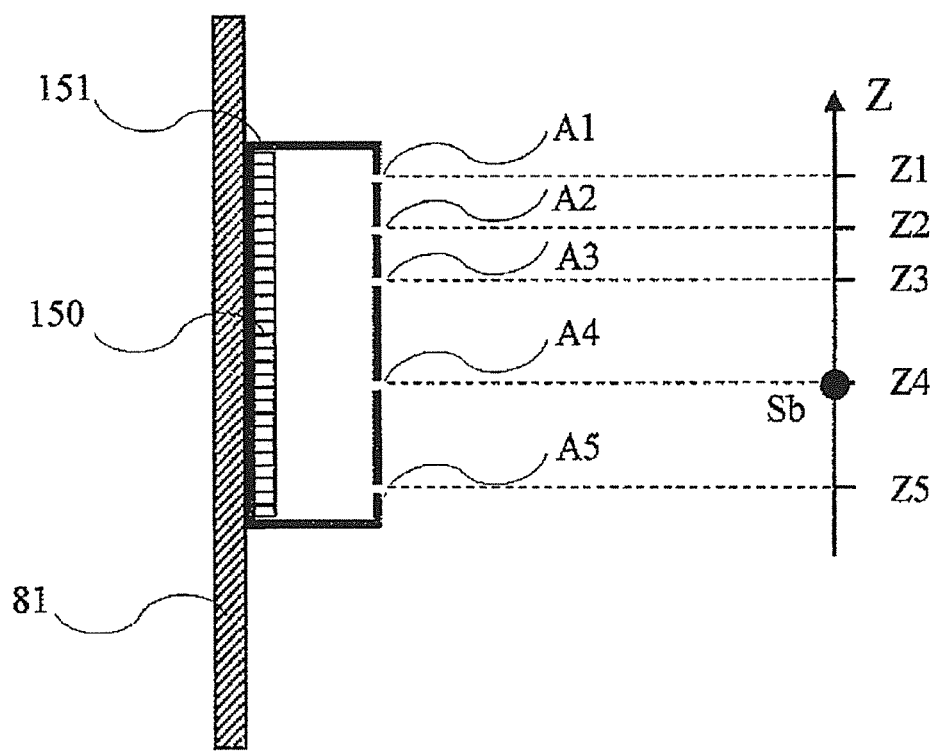
FIG. 15 illustrates an alternative configuration example of the position detection unit in the X-ray CT scanner relating to the first embodiment.
Figure 16:
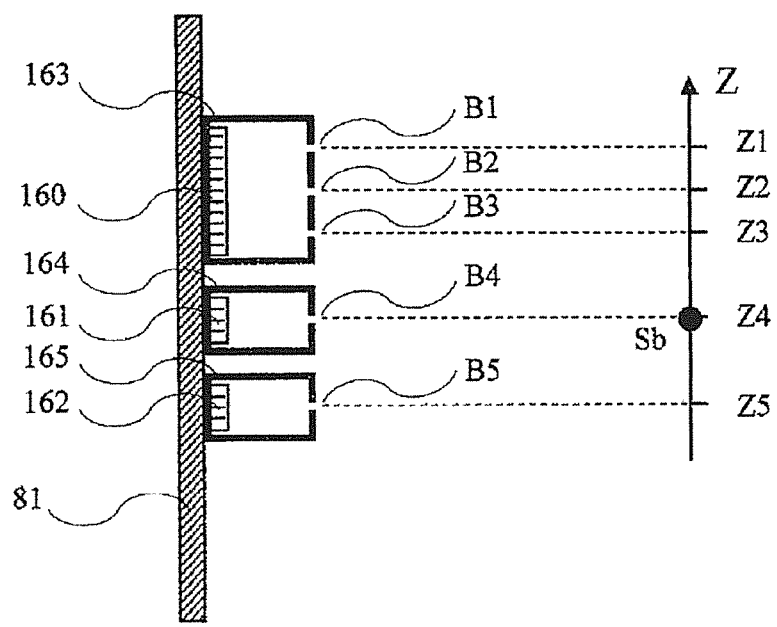
FIG. 16 illustrates an alternative configuration example of the position detection unit in the X-ray CT scanner relating to the first embodiment.
Figure 17:
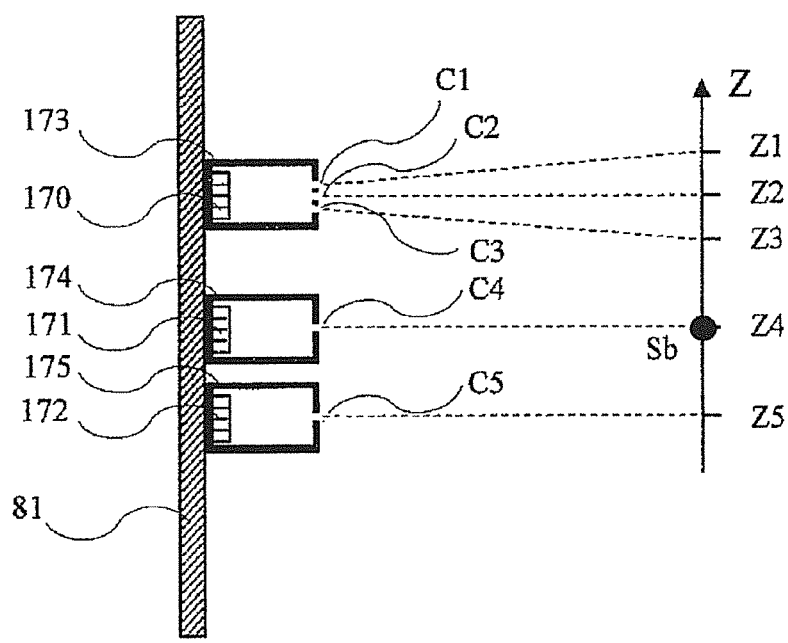
FIG. 17 illustrates an alternative configuration example of the position detection unit in the X-ray CT scanner relating to the first embodiment.

Drawings from FIG. 15 to FIG. 17 illustrate other configuration examples of the position detection unit in the X-ray CT scanner relating to the first embodiment. It is to be noted that in FIG. 15 to FIG. 17, there are shown examples assuming five different preset positions Z1 to Z5 as to the X-ray tube 1b, but the arrangement of the preset positions and the number thereof are not limited to those examples. In the example as shown in FIG. 8, the position detection units 87b1 to 87b4 are respectively arranged at the preset positions Z1 to Z4, individually, but in the example as shown in FIG. 15, the auxiliary X-ray detector 150 is commonly placed for the preset positions Z1 to Z5. A publicly known X-ray line sensor, or the like, may be employed as this kind of auxiliary X-ray detector. The auxiliary X-ray detector 150 is placed inside a common frame 151, and slits A1 to A5 are provided respectively at the Z positions corresponding to the preset positions Z1 to Z5. Using the auxiliary X-ray detector 150 commonly as described above may generate advantages such as enabling reduction of works for adjusting the arrangement and reduction of costs.

In the example as shown in FIG. 16, the auxiliary X-ray detector 160 is commonly used only for the preset positions Z1 to Z3 being relatively close to one another. There is an advantage that a relatively small-sized general-purpose X-ray array sensor, or the like, may be employed as the auxiliary X-ray detector 160. Further in the example as shown in FIG. 17, a small-sized auxiliary X-ray detector 170 is employed, instead of the auxiliary X-ray detector 160 as shown in FIG. 16. In order to implement the downsizing, slits C1 to C3 are arranged so that each of the X-ray slit images radiated from the preset positions Z1 to Z3 are formed on the auxiliary X-ray detector 170. As the auxiliary X-ray detector 170, a small-sized X-ray array sensor is used, which is identical to the auxiliary X-ray detectors 171 and 172 provided for the preset positions Z4 and Z5. With this configuration, there is an advantage that component sharing of the auxiliary X-ray detectors may reduce costs.

Figure 18:
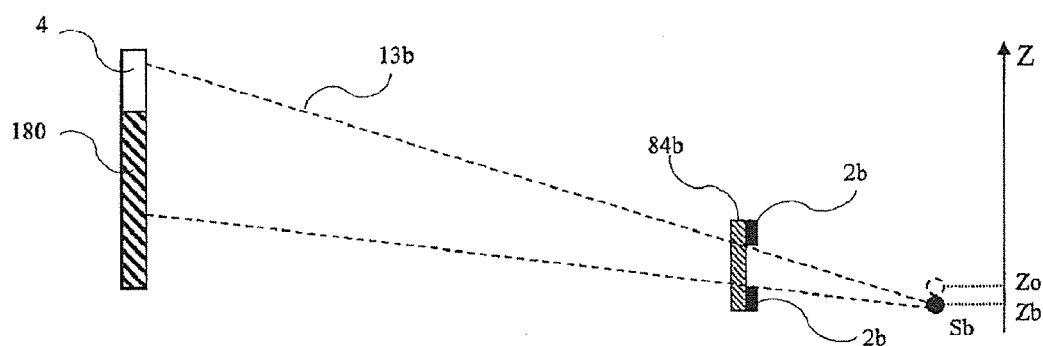
FIG. 18 illustrates a method for adjusting the positions of the collimators 2a and 2b in the X-ray CT scanner relating to the first embodiment.
Figure 19:
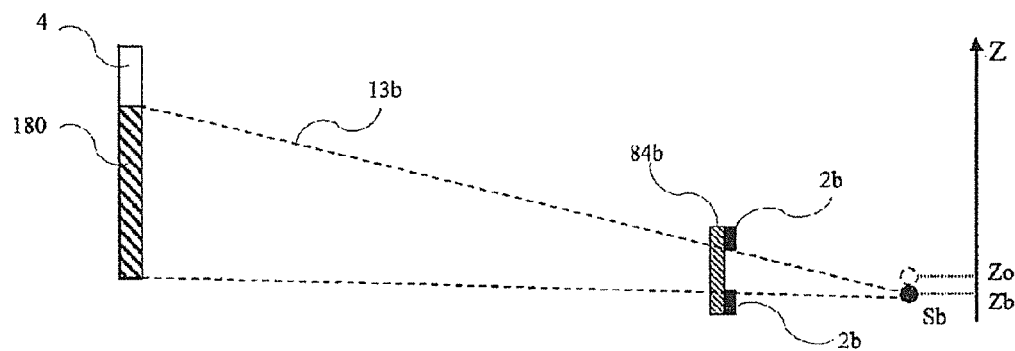
FIG. 19 illustrates a method for adjusting the positions of the collimators 2a and 2b in the X-ray CT scanner relating to the first embodiment.

FIG. 18 and FIG. 19 illustrate a method for adjusting the positions of the collimators 2a and 2b in the X-ray CT scanner relating to the first embodiment. Particularly, those figures illustrate a specific method for implementing the process of step S11 in the flowchart as shown in FIG. 10. As shown in FIG. 18, in the case where the position of the X-ray focus Sb in the Z direction is displaced from the original preset position Zo to Zb, the X-ray irradiation region 13b is displaced from the detection region 180 of the X-ray detector 4. This kind of displacement of the X-ray irradiation region 13b may expose the test subject to ineffective radiation, and it may cause an artifact within the CT image being reconstructed. Therefore, as shown in FIG. 19, the movable stage 84b modifies the position of the collimator 2b so as to coincide the X-ray irradiation region 13b with the detection region 180. Similar adjustments may also be implemented on the collimator 2a. Since the collimators 2a and 2b are lightweight relative to the X-ray tubes 1a and 1b, they are movable with relatively small force, even in the case where strong centrifugal force is applied due to the high-speed rotation of the imaging system. Therefore, a relatively small-sized drive mechanism may be used for the movable stages 84a and 84b, thereby saving space and reducing costs.

Figure 20:
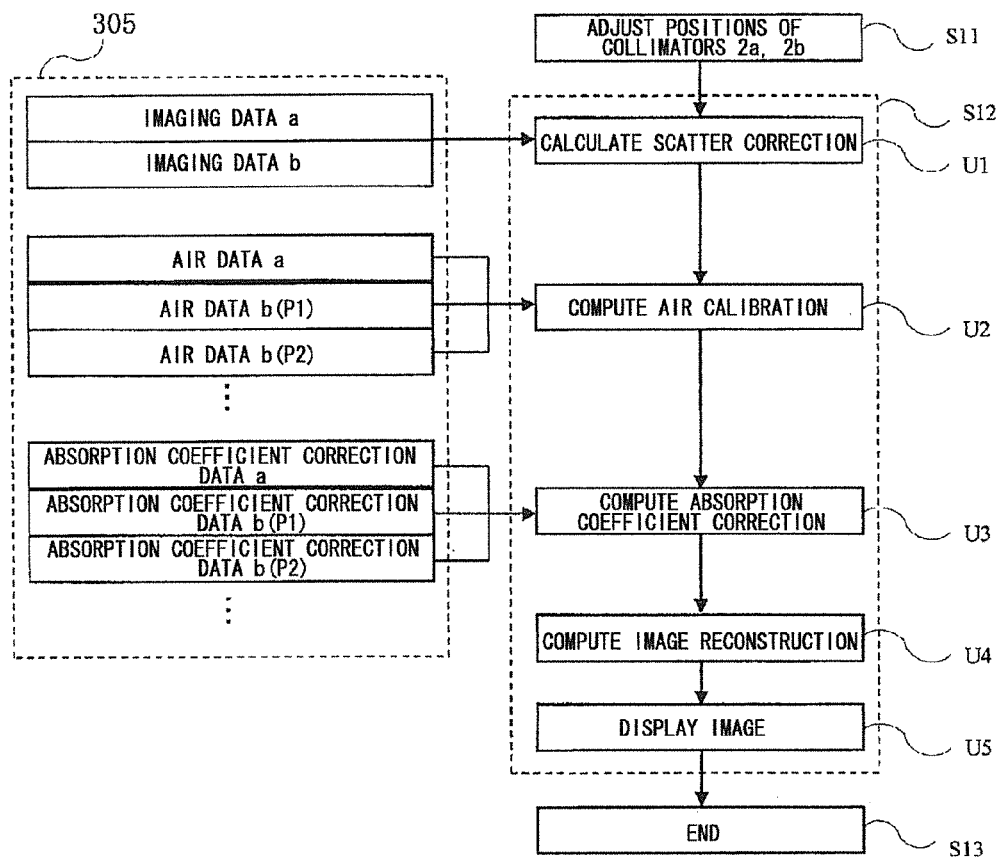
FIG. 20 is a flowchart for explaining a procedure to create a CT image in the X-ray CT scanner relating to the first embodiment.

FIG. 20 is a flowchart for explaining a procedure to create a CT image in the X-ray CT scanner relating to the first embodiment. Particularly, this figure illustrates a specific method for implementing the process of the step S12 in the flowchart as shown in FIG. 10. The imaging data items a and b detected by the X-ray detector 4, as to the x-rays alternately radiated from the X-ray tubes 1a and 1b respectively, are recorded sequentially in the memory 305. The computer 304 firstly reads the imaging data items a and b from the memory 305, and implements calculation for scatter correction (step U1). The calculation for scatter correction is to estimate and eliminate scattered X-ray components included in the imaging data items a and b, and a specific method thereof will be described in the following. Next, the computer 304 reads air data from the memory 305 and performs a publicly known computing for air calibration (step U2). It is to be noted that air data is imaging data being measured without placing the test subject 10 and recorded in advance in the memory 305 prior to imaging the test subject 10. The air data is measured as to each of the X-ray tubes 1a and 1b. In particular, as for the X-ray tube 1b, air data items b1 to b4 are measured respectively at the preset positions Z1 to Z4, and they are recorded in the memory 305. According to the preset position of the X-ray tube 1b upon imaging the test subject 10, the computer 304 reads from the memory 305, the air data b measured at the same position, and performs the computing for air calibration.

Next, the computer 304 reads absorption coefficient correction data from the memory 305, and performs a publicly known computing for the absorption coefficient correction (step U3). The absorption coefficient correction is performed for preventing fluctuations of the X-ray absorption coefficient of the test subject depending on the size thereof, due to X-ray beam hardening phenomenon. For example, a publicly known method described in the Japanese Examined Patent Application Publication No. 61-54412 may be used for acquiring correction data and performing the correcting computation. As in the case of the air data, the absorption coefficient correction data measured prior to imaging the test subject 10 is recorded in the memory 305 in advance. The absorption coefficient correction data is measured as to each of the X-ray tubes 1a and 1b, and particularly as for the X-ray tube 1b, the absorption coefficient correction data items b1 to b4 are measured respectively at the preset positions Z1 to Z4, and they are recorded in the memory 305. According to the preset position of the X-ray tube 1b upon imaging the test subject 10, the computer 304 reads from the memory 305, the absorption coefficient correction data b being measured at the same position, and performs the computing for the absorption coefficient correction. Next, the computer 304 performs the image reconstruction operation according to a publicly known method using the imaging data after the computing for the absorption coefficient correction, and creates a CT image of the test subject 10 (step U4). By way of example, the method described in the Non Patent Document 1 may be utilized as a method for the image reconstruction operation. Finally, the computer 304 displays thus created CT image on the monitor 302 by using a publicly known method (step U5).

Figure 21:
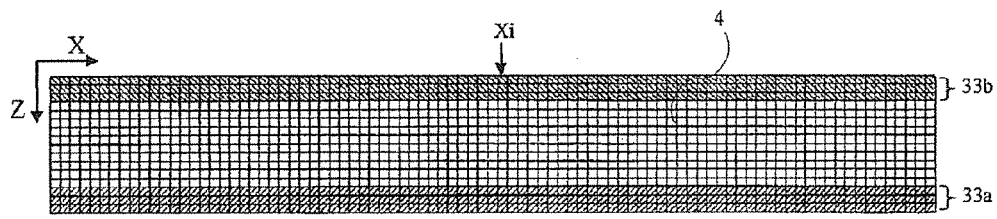
FIG. 21 illustrates the positions of non detection regions 33a and 33b, on an input plane of the X-ray detector 4 in the X-ray CT scanner relating to the first embodiment.

FIG. 21 illustrates the positions of non detection regions 33a and 33b, on the input plane of the X-ray detector 4 in the X-ray CT scanner relating to the first embodiment. As explained with reference to FIG. 5, in the multi-source mode, there are generated non detection regions 33a and 33b that the X-rays directly radiated from the X-ray tubes 1a and 1b do not enter. In the non detection regions 33a and 33b, the X-rays scattered inside test subject 10 are measured, and by using the measured data, it is possible to perform a calculation for scatter correction described in the following. It is to be noted that if the overlapped measurement region 50 as shown in FIG. 5 is maximized, the area of the non detection regions 33a and 33b becomes zero, resulting in failing to measure the scatter data. Therefore, when the scatter correction is performed, it is necessary to reserve in advance, regions of around five pixels in the Z direction, for instance, respectively as the non detection regions 33a and 33b at the minimum.

Figure 22:
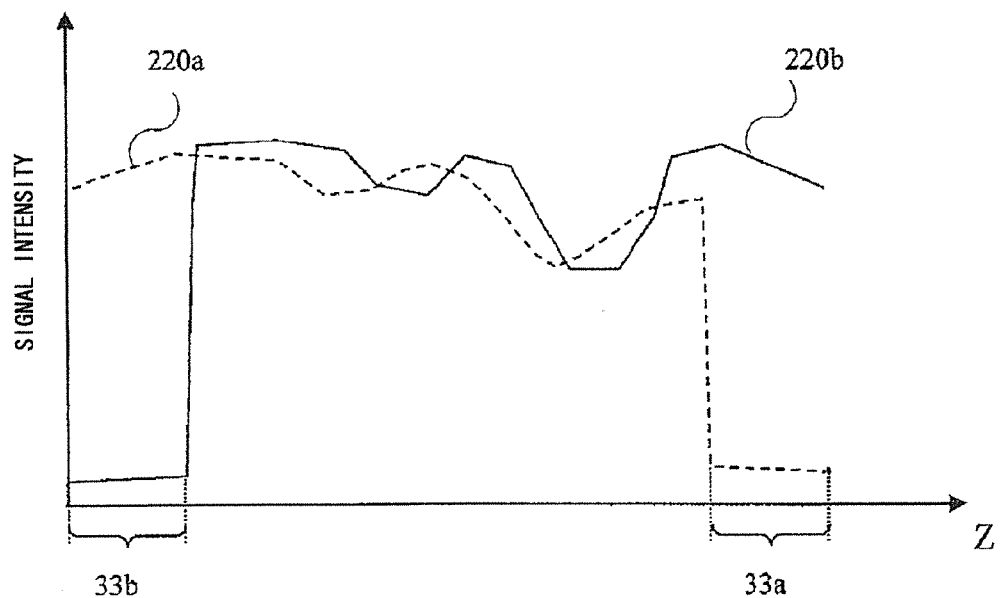
FIG. 22 illustrates an example of profiles 220a and 220b in the Z axis direction of the measurement signals of the X-ray detector 4 in the X-ray CT scanner relating to the first embodiment.
Figure 23:
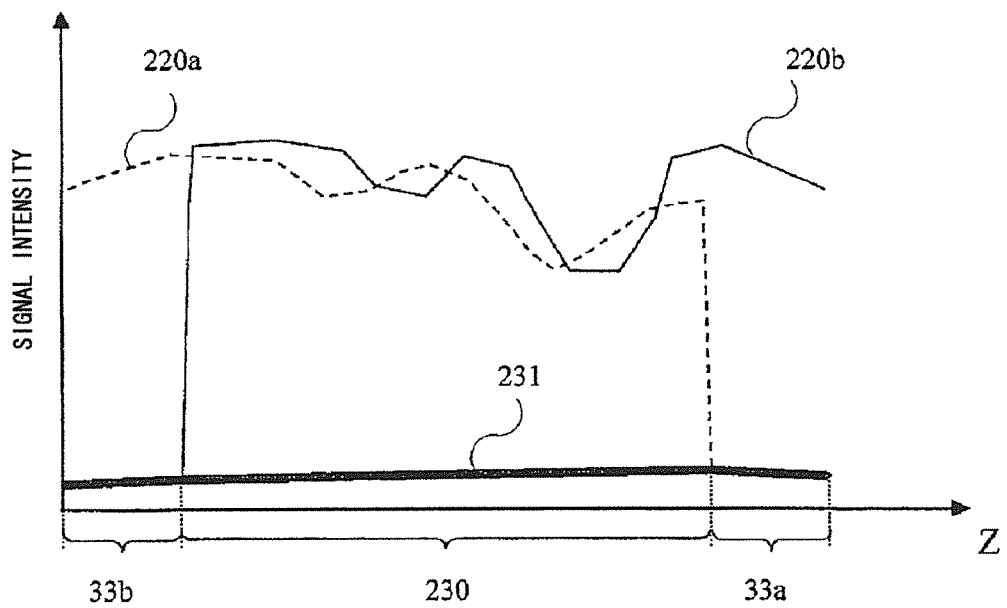
FIG. 23 illustrates a method for estimating a scattered X-ray distribution 231 based on the profiles 220a and 220b.

FIG. 22 illustrates an example of profiles 220a and 220b in the Z axis direction of the measurement signals of the X-ray detector 4 in the X-ray CT scanner relating to the first embodiment. FIG. 23 illustrates a method for estimating a scattered X-ray distribution 231 based on the profiles 220a and 220b. Particularly, FIG. 23 illustrates a specific method for implementing the process of the step U1 in the flowchart as shown in FIG. 20. In FIG. 22, a signal in the non detection region 33a corresponds to the scattered X-ray signal, as to the profile 220a of the X-rays radiated from the X-ray tube 1a. On the other hand, a signal in the non detection region 33b corresponds to the scattered X-ray signal, as to the profile 220b of the X-rays radiated from the X-ray tube 1b. Here, the distribution in the Z direction of the scattered X-rays have a property which fluctuates relatively gently and if this property is utilized, it is possible to estimate the scattered X-ray profile 231 in the region 230, other than the aforementioned non detection regions 33a and 33b, by linearly interpolating in the Z direction the signals measured in the non detection regions 33a and 33b, or the like. Thus obtained scattered X-ray profile 231 is subtracted from each of the profiles 220a and 220b, thereby allowing the scatter correction to be carried out. In addition, the aforementioned scatter correction is performed at all pixel positions xi in the X direction as shown in FIG. 21.

As described above, in the X-ray CT scanner relating to the first embodiment, since the position of the X-ray tube 1b can be variously changed in the Z direction, there are effects such as changing the imaging field of view in the Z direction in the multi-source mode imaging, and expanding the imaging field of view in the Z direction in the single source mode imaging. During the imaging preparation period, the imaging system is rotated at low speed and the centrifugal force applied on the X-ray tube 1b is kept down, thereby allowing a high speed shifting of the X-ray tube 1b, also enabling the low-speed rotation to be immediately transferred to the high-speed rotation. Therefore, there is an effect that the imaging preparation period is reduced, and accordingly the examination throughput is enhanced. In addition, positions of the X-ray focuses Sa and Sb are monitored by using the position detection unit 87, it is possible to modify the position of the X-ray tube 1b during the imaging preparation period, and modify the positions of the collimators 2a and 2b during the imaging period. Therefore, there are effects that exposure of the test subject 10 to ineffective radiation is reduced, as well as reducing the generation of artifact in the CT image.

Second Embodiment

Since a major configuration of the X-ray CT scanner relating to the second embodiment is the same as the first embodiment, the X-ray CT scanner relating to the second embodiment will be explained, focusing on different points.

Figure 24:
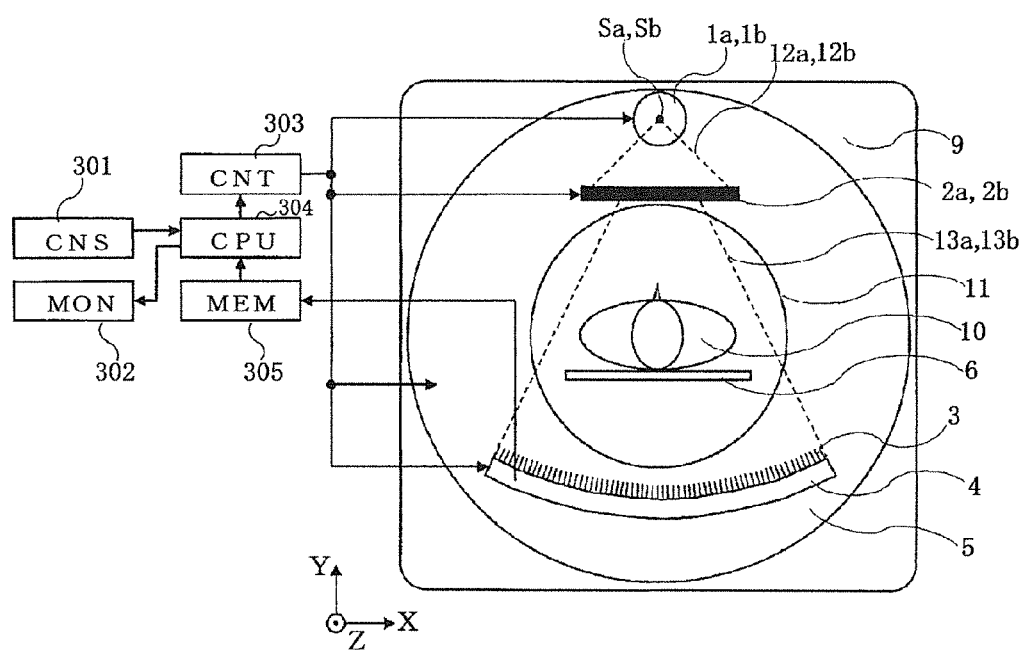
FIG. 24 is a front schematic view of the X-ray CT scanner relating to a second embodiment of the present invention.

FIG. 24 is a front schematic view of the X-ray CT scanner relating to a second embodiment of the present invention. Since the major configuration of the X-ray CT scanner is identical to the X-ray CT scanner as shown in FIG. 1 in the first embodiment, tedious explanations will not be made. A different point is that the slit 7 and the auxiliary X-ray detector 8 do not exist for the present X-ray CT scanner, which are used to measure position displacement in the Z direction of the X-ray focuses Sa and Sb. In the present X-ray CT scanner, instead of tolerating the displacements in the Z direction of the X-ray focuses Sa and Sb, the positions of the collimators 2a and 2b are modified, thereby keeping the X-ray irradiation region 13 to be a constant position with respect to the X-ray detector 4. As described in the following, an adequate modification amount of the collimators 2a and 2b positions is calculated based on the detection signal from the X-ray detector 4. Therefore, in the present X-ray CT scanner, it is possible to eliminate the slit 7 and the auxiliary X-ray detector 8 used in the first embodiment, and also the position detection unit 87 made up of those elements above and the position detection unit supporting frame 86, and the like, and thus there are advantages such as reduction of works for adjusting the arrangement of the elements above and reduction of costs needed for manufacturing those elements.

Figure 25:
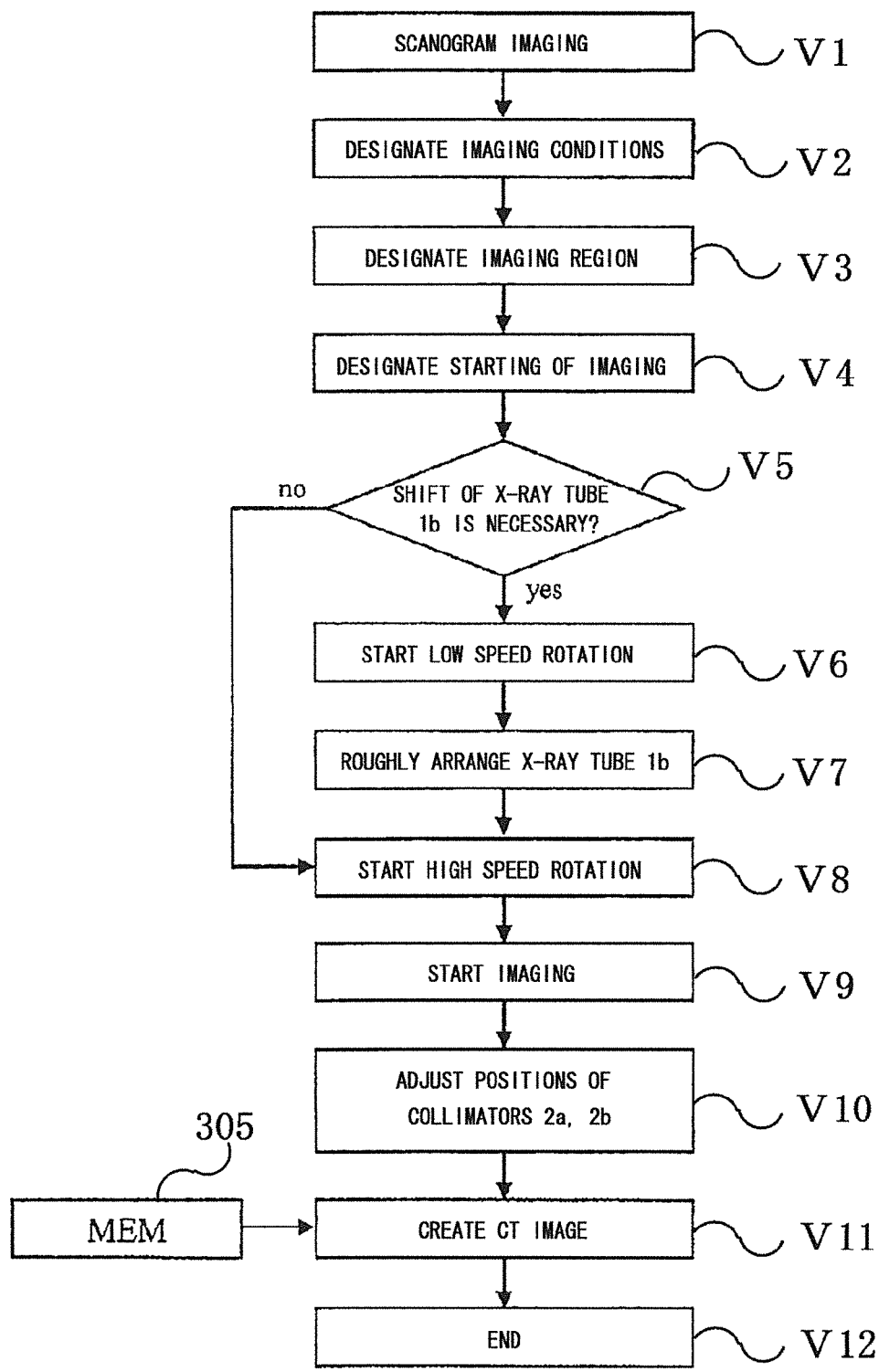
FIG. 25 is a flowchart for explaining an imaging procedure of the X-ray CT scanner relating to the second embodiment.

FIG. 25 is a flowchart for explaining an imaging procedure of the X-ray CT scanner relating to the second embodiment. Since most of the imaging procedure of the X-ray CT scanner is identical to the imaging procedure as shown in FIG. 10 in the first embodiment, tedious explanations will not be made. A different point is that position adjustment of the X-ray tube 1b (step S8) performed in FIG. 10 is omitted in the imaging procedure of the present X-ray CT scanner. In other words, immediately after completing the rough arrangement of the X-ray tube 1b (step V7), high-speed rotation of the imaging system is started (step V8), and thereafter imaging is started (step V9). During the imaging, position adjustment of the collimators 2a and 2b is performed according to the method described in the following (step V10). Since the position adjustment of the X-ray tube 1b is omitted, there is a possibility that the position of the X-ray irradiation region 13 just after starting the imaging may be deviated from a predetermined adequate position on the X-ray detector 4. However, the position is immediately modified in the step V10, thereby controlling the exposure of the test subject 10 to ineffective radiation and generation of artifact in the CT image to be the minimum. In addition, since the position adjustment of the X-ray tube 1b is omitted, there is an effect that the imaging preparation period is reduced and therefore the examination throughput is enhanced.

Figure 26:
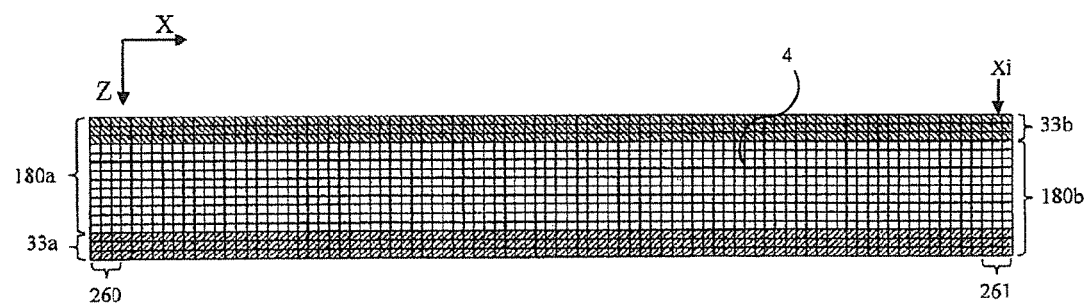
FIG. 26 illustrates positions of displacement detection regions 260 and 261 that are provided on the input plane of the X-ray detector 4, so as to measure a position displacement amount of the collimators 2a and 2b in the Z axis direction, in the X-ray CT scanner relating to the second embodiment.

FIG. 26 illustrates positions of displacement detection regions 260 and 261 which are provided on the input plane of the X-ray detector 4, so as to measure a position displacement amount of the collimators 2a and 2b in the Z axis direction, in the X-ray CT scanner relating to the second embodiment. As illustrated in the figure, the displacement detection regions 260 and 261 are provided respectively on both ends of the X-ray detector 4 in the X direction. Typically, the imaging FOV size of the X-ray detector 4 is designed sufficiently large relative to the test subject 10, and therefore, also at the time of imaging the test subject 10, air data is measured in the displacement detection regions 260 and 261. Therefore, by using the air data, it is possible to measure the position displacement amount of the collimators 2a and 2b, without the auxiliary x-ray detector that is used the first embodiment. It is to be noted that the position displacement amount is calculated based on a shift amount on the edge of the X-ray irradiation region 13 in the Z direction, being measured in proximity to the boundary between the detection region 180a and the non detection region 33a, and between the detection region 180b and the non detection region 33b. Therefore, in order to measure the position displacement amount of the collimators 2a and 2b, it is necessary to reserve in advance, regions of around five pixels in the Z direction, for instance, respectively as the non detection regions 33a and 33b at the minimum.

Figure 27:
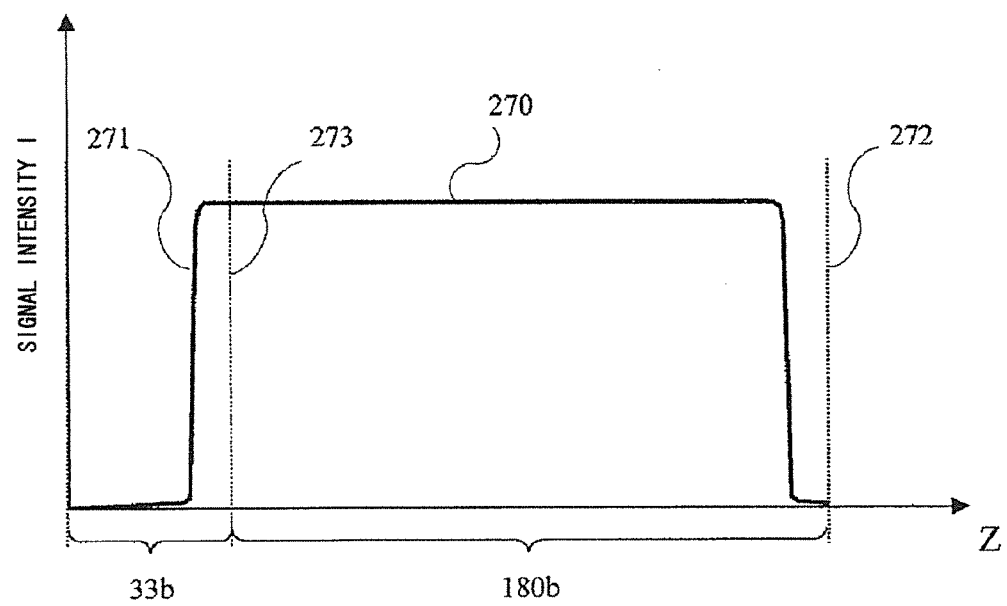
FIG. 27 illustrates an example of the profile 270 of air data in the Z direction, being measured in the displacement detection regions 260 and 261 on the X-ray detector 4, in the X-ray CT scanner relating to the second embodiment.

FIG. 27 illustrates an example of the profile 270 of the air data in the Z direction, being measured in the displacement detection regions 260 and 261 on the X-ray detector 4, in the X-ray CT scanner relating to the second embodiment. It is to be noted that the profile 270 is calculated as an average value of the profile that is measured at all the pixel positions Xi in the X direction, belonging to the displacement detection regions 260 and 261. Further this figure illustrates an example of the imaging data as to the X-ray tube 1b, in particular. When the position displacement occurs in the Z direction at the X-ray focus Sb, as explained with reference to FIG. 18, the X-ray irradiation region 13 is made to shift in the Z direction. On this occasion, the edge 271 of the X-ray irradiation region 13 within the profile 270 is displaced with respect to the boundary 273 between the non detection regions 33b and the detection region 180, it is possible to calculate an amount to be modified to reach an adequate position of the collimator 2b, according to the method as described in the following.

Figure 28:
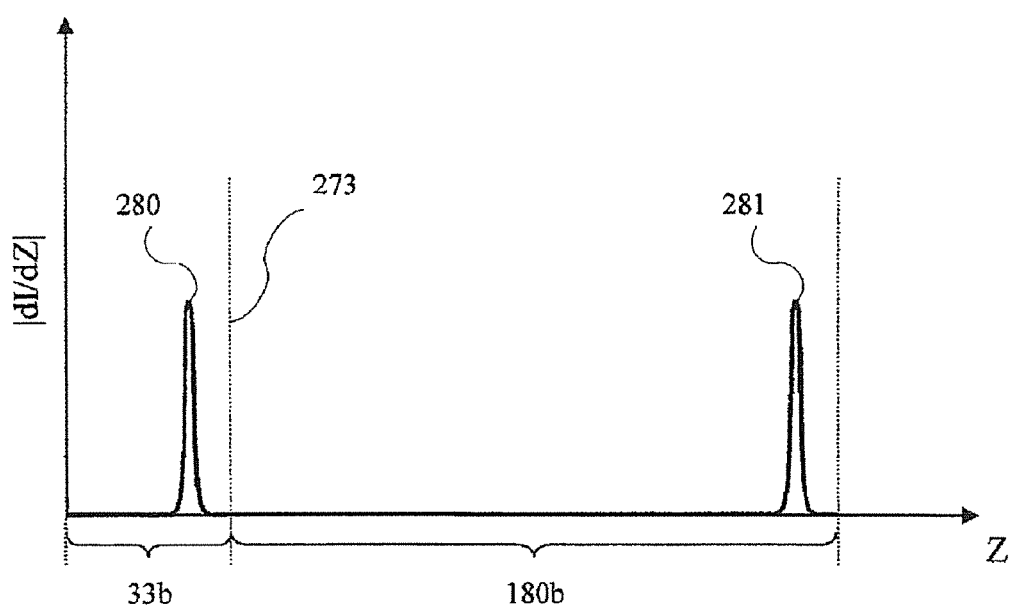
FIG. 28 illustrates an absolute value of first derivation in the Z direction of the profile 270 as shown in FIG. 27.

FIG. 28 illustrates an absolute value of first derivation in the Z direction of the profile 270 as shown in FIG. 27. As illustrated in the figure, an absolute value of the first derivation is calculated, and accordingly, the signal peaks 280 and 281 are generated respectively at the edges 271 and 272 of the X-ray irradiation region 13. Therefore, the barycentric position ZG of each of the signal peaks are assumed as the aforementioned edges 271 and 272. The formula 2 is used for calculating the barycentric position ZG. It is to be noted here that in the formula 2, ZP0 is assumed as the boundary 273 and the sample number of counts n of the measured data items is changed to the sample number of counts being appropriate in proximity to the boundary 273. If the barycentric position ZG is obtained, a modification amount AZ to get to the adequate position of the collimator 2b can be calculated according to the formula 1. Here, it is to be noted that in the formula 1, DX represents a distance in the X direction between the X-ray focus Sb and the collimator 2b, and dX represents a distance in the X direction between the X-ray focus Sb and the input plane of the X-ray detector 4. It is further possible to calculate, also as to the X-ray focus Sa, the modification amount AZ to get to the adequate position of the collimator 2a, according a similar manner.

As discussed above, in the X-ray CT scanner relating to the second embodiment, it is possible to eliminate constitutional elements such as the position detection unit 87, and the like, being used in the X-ray CT scanner as described in the first embodiment, and there are effects such as reduction of works for adjusting the arrangement of such elements above and reduction of costs needed for manufacturing those elements. There is another effect that the time required for the imaging preparation period is reduced, thereby further enhancing the examination throughput.

Although only some exemplary embodiments of the present invention have been described above, many modifications are possible in the exemplary embodiments without materially departing from the scope of the invention. By way of example, the aforementioned first and second embodiments illustrate a configuration where only the X-ray focus Sb is shifted in the Z direction, but both the X-ray focus Sa and Sb may be shifted. On this occasion, shifting of two X-ray focuses simultaneously may generate an advantage that shifting time is reduced. In addition, a multi-source CT having two pairs of the X-ray source and the X-ray detector as described in the Patent document 3, may be provided with a mechanism for shifting the X-ray tube while rotating at a low speed as described in the present invention.

EXPLANATION OF REFERENCES

1 . . . X-ray tube
2 . . . collimator
3 . . . anti-scatter collimator
4 . . . X-ray detector
5 . . . rotating plate
6 . . . bed board
7 . . . slit
8 . . . auxiliary X-ray detector
9 . . . gantry
10 . . . test subject
11 . . . opening
12 . . . X-ray irradiation region
13 . . . X-ray irradiation region
301 . . . console (CNS)
302 . . . monitor (MON)
303 . . . controller (CNT)
304 . . . computer (CPU)
305 . . . memory (MEM)
30 . . . imaging region
31 . . . measurement region
32 . . . non measurement region
33 . . . non detection region
80 . . . drum-type frame
81 . . . position detection unit supporting frame
82 . . . hole
83 . . . hole
84 . . . movable stage
85 . . . movable stage
86 . . . X-ray tube supporting frame
87 . . . position detection unit
88 . . . beam compensation filter
110 . . . scanogram image
111 . . . imaging candidate region
180 . . . detection region
260 . . . displacement detection region
261 . . . displacement detection region

What is claimed is:
1. An X-ray CT scanner comprising,
multiple X-ray generators,
a collimator for restricting an irradiation range of X-rays radiated from the X-ray generators,
at least one X-ray detector for detecting the X-rays whose irradiation range is restricted,
an auxiliary X-ray detector, a supporter for supporting the X-ray generators and the X-ray detector, a rotation mechanism for rotating the supporter about a rotation axis, a shifting mechanism for shifting in a direction of the rotation axis, a position of at least one X-ray generator out of the multiple X-ray generators, with respect to the supporter, and a signal processor for applying signal processing on a signal detected by the X-ray detector, wherein the shifting mechanism is adapted to change a position of the X-ray generator to a selected one of a multiple preset positions, and wherein the auxiliary X-ray detector is adapted to detect the X-rays radiated from the X-ray generator in proximity to the selected preset position, whereby an amount of displacement from the selected preset position of the X-ray generator is calculated based on a detection signal of the auxiliary X-ray detector, and wherein the position of the X-ray generator is modified based on the amount of displacement.

2. The X-ray CT scanner according to claim 1, further comprising a function for keeping a speed of rotation by the rotation mechanism, to a predetermined value or less, during a period of shifting by the shifting mechanism.

3. The X-ray CT scanner according to claim 1, further comprising a function for designating an imaging region of a test subject prior to imaging, and a function for automatically selecting a preset position which implements a minimum imaging field of view covering the imaging region, out of the multiple preset positions.

4. The X-ray CT scanner according to claim 1, further comprising a recording part for recording an X-ray calibration signal measured in advance at the selected preset position of the X-ray generator.

5. The X-ray CT scanner according to claim 1, further comprising a function for blocking X-ray irradiation on a test subject, by closing the collimator until the amount of displacement becomes smaller than a predetermined value.

6. The X-ray CT scanner according to claim 1, wherein the auxiliary X-ray detector is provided at each of the multiple preset positions.

7. The X-ray CT scanner according to claim 1, wherein the auxiliary X-ray detector is provided commonly for a part of or all of the multiple preset positions.

8. An X-ray CT scanner comprising, multiple X-ray generators, a collimator for restricting an irradiation range of X-rays radiated from the X-ray generators, at least one X-ray detector for detecting the X-rays whose irradiation range is restricted, an auxiliary X-ray detector, a supporter for supporting the X-ray generators and the X-ray detector, a rotation mechanism for rotating the supporter about a rotation axis, a shifting mechanism for shifting in a direction of the rotation axis, a position of at least one X-ray generator out of the multiple X-ray generators, with respect to the supporter, and a signal processor for applying signal processing on a signal detected by the X-ray detector, wherein the shifting mechanism is adapted to change a position of the X-ray generator to a selected one of a multiple preset positions, and wherein the auxiliary X-ray detector is adapted to detect the X-rays radiated from the X-ray generator in proximity to the selected preset position, whereby an amount of displacement from the selected preset position of the X-ray generator is calculated based on a detection signal of the auxiliary X-ray detector, and wherein the position of the collimator is modified based on the amount of displacement, so that an irradiation range of the X-rays radiated from the X-ray generator on the X-ray detector is placed at a predetermined position.

9. The X-ray CT scanner according to claim 8, further comprising a function for designating an imaging region of a test subject prior to imaging, and a function for automatically selecting a preset position which implements a minimum imaging field of view covering the imaging region, out of the multiple preset positions.

10. The X-ray CT scanner according to claim 8, further comprising a recording part for recording an X-ray calibration signal measured in advance at the selected preset position of the X-ray generator.

11. An X-ray CT scanner comprising, multiple X-ray generators, a collimator for restricting an irradiation range of X-rays radiated from the X-ray generators, at least one X-ray detector for detecting the X-rays whose irradiation range is restricted, a supporter for supporting the X-ray generators and the X-ray detector, a rotation mechanism for rotating the supporter about a rotation axis, a shifting mechanism for shifting in a direction of the rotation axis, a position of at least one X-ray generator out of the multiple X-ray generators, with respect to the supporter, and a signal processor for applying signal processing on a signal detected by the X-ray detector, wherein the shifting mechanism is adapted to change a position of the X-ray generator to a selected one of a multiple preset positions, and wherein the position of the collimator is controlled so that a non-irradiation range is provided in a part of the X-ray irradiation range in which a test subject is irradiated in overlapped manner by the multiple X-ray generators, the X-ray CT scanner further comprising a function for calculating an amount of displacement of the position of the X-ray generator from the selected preset position, based on signals detected respectively in the X-ray irradiation range and in the non-irradiation range on the X-ray detector, and a function for modifying the position of the X-ray generator based on the amount of displacement.

12. An X-ray CT scanner comprising, multiple X-ray generators, a collimator for restricting an irradiation range of X-rays radiated from the X-ray generators, at least one X-ray detector for detecting the X-rays whose irradiation range is restricted, a supporter for supporting the X-ray generators and the X-ray detector, a rotation mechanism for rotating the supporter about a rotation axis, a shifting mechanism for shifting in a direction of the rotation axis, a position of at least one X-ray generator out of the multiple X-ray generators, with respect to the supporter, and a signal processor for applying signal processing on a signal detected by the X-ray detector, wherein the shifting mechanism is adapted to change a position of the X-ray generator to a selected one of a multiple preset positions, and wherein the position of the collimator is controlled so that a non-irradiation range is provided in a part of the X-ray irradiation range in which a test subject is irradiated in overlapped manner by the multiple X-ray generators, the X-ray CT scanner further comprising a function for calculating an amount of displacement of the position of the X-ray generator from the selected preset position, based on signals detected respectively in the X-ray irradiation range and in the non-irradiation range on the X-ray detector, and a function for modifying the position of the collimator based on the amount of displacement, so that the X-ray irradiation range radiated from the X-ray generator to the X-ray detector is placed at a predetermined position.

13. An X-ray CT scanner comprising, multiple X-ray generators, a collimator for restricting an irradiation range of X-rays radiated from the X-ray generators, at least one X-ray detector for detecting the X-rays whose irradiation range is restricted, a supporter for supporting the X-ray generators and the X-ray detector, a rotation mechanism for rotating the supporter about a rotation axis, a shifting mechanism for shifting in a direction of the rotation axis, a position of at least one X-ray generator out of the multiple X-ray generators, with respect to the supporter, and a signal processor for applying signal processing on a signal detected by the X-ray detector, wherein a position of the collimator restricting the X-ray irradiation range is controlled so that a non-irradiation range is provided in a part of the X-ray irradiation range in which a test subject is irradiated in overlapped manner by the multiple X-ray generators, and a function for calculating and eliminating an amount of scattered X-ray component included in the signal detected in the X-ray irradiation range, based on the signal detected in the non-irradiation range, out of the detection signals of the X-ray detector.

* * * * *